US009783528B2

(12) United States Patent
Harbeson

(10) Patent No.: US 9,783,528 B2
(45) Date of Patent: Oct. 10, 2017

(54) INHIBITORS OF THE ENZYME UDP-GLUCOSE: N-ACYL-SPHINGOSINE GLUCOSYLTRANSFERASE

(71) Applicant: Concert Pharmaceuticals, Inc., Lexington, MA (US)

(72) Inventor: Scott L. Harbeson, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 14/853,900

(22) Filed: Sep. 14, 2015

(65) Prior Publication Data

US 2016/0068519 A1 Mar. 10, 2016

Related U.S. Application Data

(63) Continuation-in-part of application No. PCT/US2014/021984, filed on Mar. 7, 2014.

(60) Provisional application No. 61/788,946, filed on Mar. 15, 2013.

(51) Int. Cl.
*A61K 31/40* (2006.01)
*C07D 405/10* (2006.01)
*C07D 403/06* (2006.01)
*C07B 59/00* (2006.01)

(52) U.S. Cl.
CPC .......... *C07D 405/10* (2013.01); *C07B 59/002* (2013.01); *C07D 403/06* (2013.01); *C07B 2200/05* (2013.01)

(58) Field of Classification Search
USPC .............................. 514/422, 228.8, 359, 408
See application file for complete search history.

(56) References Cited

U.S. PATENT DOCUMENTS

| | | |
|---|---|---|
| 6,221,335 B1 | 4/2001 | Foster |
| 6,440,710 B1 | 8/2002 | Keinan et al. |
| 6,603,008 B1 | 8/2003 | Ando et al. |
| 7,517,990 B2 | 4/2009 | Ito et al. |
| 7,615,573 B2 * | 11/2009 | Siegel ............... A61K 31/4025 514/422 |
| 2001/0041735 A1 | 11/2001 | Shayman et al. |
| 2007/0082929 A1 | 4/2007 | Gant et al. |
| 2007/0197695 A1 | 8/2007 | Potyen et al. |
| 2007/0203223 A1 | 8/2007 | Siegel et al. |
| 2008/0103122 A1 | 5/2008 | Veltri |
| 2011/0166134 A1 | 7/2011 | Ibraghimov-Beskrovnaya et al. |
| 2011/0184021 A1 | 7/2011 | Siegel et al. |

FOREIGN PATENT DOCUMENTS

| | | |
|---|---|---|
| WO | WO 95/26325 | 10/1995 |
| WO | WO 2007/118651 | 10/2007 |

OTHER PUBLICATIONS

Kushner; Canadian Journal of Physiology and Pharmacology; 1999, 77, 79-88.*
International Search Report and Written Opinion in International Application No. PCT/US2014/021984, dated Jun. 23, 2014, 14 pages.
International Preliminary Report on Patentability in International Application No. PCT/US2014/021984, dated Sep. 15, 2015, 6 pages.
Baillie, "The Use of Stable Isotopes in Pharmacological Research," *Pharmacology Rev*, 1981, 33(2):81-132.
Blake et al., "Studies with deuterated drugs," J. Pharm Sci, 1975, 64:367-391.
Browne, "Stable Isotope Techniques in Early Drug Development: An Economic Evaluation," *J. Clin. Pharmacology*, 1998, 38: 213-20.
Cerdelga, Highlights of Prescribing Information, Genzyme Corporation, revised Aug. 2014, 22 pages.
Cherrah et al., "Study of Deuterium Isotope Effects on Protein Binding by Gas Chromatography/Mass Spectrometry. Caffeine and Deuterated Isotopomers," *Biomed. and Environmental Mass Spectrometry*, 1987, 14: 653-57.
Dyck et al., "Effects of Deuterium Substitution on the Catabolism of β-Phenylethylamine: An In Vivo Study," *J. Neurochemistry*, 1986, 46: 399-404.
Fisher et al., "The complexities inherent in attempts to decrease drug clearance by blocking sites of CYP-mediated metabolism," *Curr. Opin. Drug Discov. Dev.*, 2006, 9(1):101-109.
Foster, "Deuterium isotope effects in studies of drug metabolism," *Trends in Pharmaceutical Sciences*, 1984, 524-527.
Foster, "Deuterium Isotope Effects in the Metabolism of Drugs and Xenobiotics: Implications for Drug Design," *Adv. Drug Res.*, 1985, 14: 2-40.
Fukuto et al."Determination of the mechanism of demethylenation of (methylenedioxy)phenyl compounds by cytochrome P450 using deuterium isotope effects," *J. Med Chem*, 1991, 34:2871-2876.
Gouyette, "Synthesis of Deuterium-labelled Elliptinium and its Use in Metabolic Studies," *Biomed. and Environmental Mass Spectrometry*, 1988, 15: 243-47.
Haskins, "The Application of Stable Isotopes in Biomedical Research," *Biomed. Spectrometry*, 1982, 9(7):269-77.
Honma et al., "The Metabolism of Roxatidine Acetate Hydrochloride," *Drug Metab. Dispos*, 1987, 15(4): 551-559.
Houston et al., "Prediction of hepatic clearance from microsomes, hepatocytes, and liver slices," Drug Metab Rev, 1997, 29:891-922.
Houston, "Utility of in vitro drug metabolism data in predicting in vivo metabolic clearance," Biochem Pharmacol, 1994, 47:1469.
Iwatsubo et al., "Prediction of in vivo drug metabolism in the human liver from in vitro metabolism data," Pharmacol Ther, 1997, 73:147-171.
Kushner et al. "Pharmacological uses and perspectives of heavy water and deuterated compounds," *Can. J. Physiol. Pharmacol.* 1999, 77: 79-88.
Lave et al., "The use of human hepatocytes to select compounds based on their expected hepatic extraction ratios in humans," Pharm Res, 1997, 14:152-155.

(Continued)

*Primary Examiner* — Pancham Bakshi
(74) *Attorney, Agent, or Firm* — Fish & Richardson P.C.

(57) ABSTRACT

This invention relates to novel inhibitors of UDP-glucose: N-acyl-sphingosine glucosyltransferase and pharmaceutically acceptable salts thereof. This invention also provides compositions comprising a compound of this invention and the use of such compositions in methods of treating diseases and conditions that are beneficially treated by administering inhibitors of UDP-glucose: N-acyl-sphingosine glucosyltransferase.

20 Claims, No Drawings

(56) References Cited

OTHER PUBLICATIONS

Obach, "Prediction of human clearance of twenty-nine drugs from hepatic microsomal intrinsic clearance data: An examination of in vitro half-life approach and nonspecific binding to microsomes," Drug Metab Disp, 1999, 27:1350-1359.

Pieniaszek et al., "Moricizine bioavailability via simultaneous, dual, stable isotope administrations: bioequivalence," *J. Clin. Pharmacology*, 1999, 39:817-25.

Tonn et al., "Simultaneous Analysis of Diphenhydramine and a Stable Isotope Analog ($^2$H10) Diphenhydramine Using Capillary Gas Chromatography with Mass Selective Detection in Biological Fluids from Chronically Instrumented Pregnant Ewes," *Biol. Mass Spectrometry*, 1993, 22:633-642.

Wolen, "The Application of Stable Isotopes to Studies of Drug Bioavailability and Bioequivalence," *J. Clin. Pharmacology*, 1986, 26:419-424.

Dumont et al., "Prospects in the use of deuterated molecules as therapeutic agents," Revue IRE Tijdschrift, Jan. 1, 1982, 6(4):2-10 (English translation of article's conclusions).

Extended European Search Report in corresponding European Application No. 14767862.7, dated Oct. 7, 2016, 7 pages.

\* cited by examiner

INHIBITORS OF THE ENZYME UDP-GLUCOSE: N-ACYL-SPHINGOSINE GLUCOSYLTRANSFERASE

CROSS-REFERENCE TO RELATED APPLICATIONS

This application is a continuation-in-part of PCT Application No. PCT/US2014/021984, filed Mar. 7, 2014, which claims the benefit of U.S. Provisional Application Ser. No. 61/788,946, filed Mar. 15, 2013. The disclosure of the prior applications are considered part of (and are incorporated by reference in) the disclosure of this application.

FIELD OF THE INVENTION

This invention relates to inhibitors of the enzyme UDP-glucose: N-acyl-sphingosine glucosyltransferase and pharmaceutically acceptable salts thereof. This invention also provides compositions comprising a compound of this invention and the use of such compositions in methods of treating diseases and conditions that are beneficially treated by administering an inhibitor of the above enzyme.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

Eliglustat, also known by the chemical name, N-[2-(2,3-dihydro-1,4-benzodioxin-6-yl)-2(R)-hydroxy-1(R)-(pyrrolidin-1-ylmethyl)ethyl]octanamide, is an inhibitor of the enzyme UDP-glucose: N-acyl-sphingosine glucosyltransferase. It may be used for the treatment of diseases such as Tay-Sach's, Gaucher's and Fabry's diseases, which are characterized by the accumulation of glycosphingolipids. Currently, eliglustat is undergoing phase 3 clinical evaluation for Gaucher's disease.

Despite the beneficial activities of eliglustat, there is a continuing need for new compounds to treat the aforementioned diseases and conditions.

DETAILED DESCRIPTION OF THE INVENTION

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of eliglustat will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 55% of the compound. In other embodiments, the relative amount of such isotopologues in toto will be less than 50%, less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methylamine, N-ethylamine; diethylamine; triethylamine; mono-, bis-, or tris-(2-OH—(C$_1$-C$_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

The compounds of the present invention (e.g., compounds of Formula I, Ia, Ib and Ic), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "d$_{x-y}$" refers to substitution with from x to y number of deuterium atoms. "Stereoisomer" refers to both enantiomers and diastereomers. "Tert" and "t-" each refer to tertiary. "US" refers to the United States of America.

A group is "substituted with" a substituent when one or more hydrogen atoms of the group are replaced with a corresponding number of substituent atoms (if the substituent is an atom) or groups (if the substituent is a group). For example, "substituted with deuterium" refers to the replacement of one or more hydrogen atoms with a corresponding number of deuterium atoms.

Throughout this specification, a variable may be referred to generally (e.g., "each Y", "each X", etc.) or may be referred to specifically (e.g., "Y$^1$, Y$^2$, Y$^3$, . . . ", "X$^1$, X$^2$, X$^3$, . . . " etc.). Unless otherwise indicated, when a variable is referred to generally, it is meant to include all specific embodiments of that particular variable.

Therapeutic Compounds

The present invention provides a compound of Formula I:

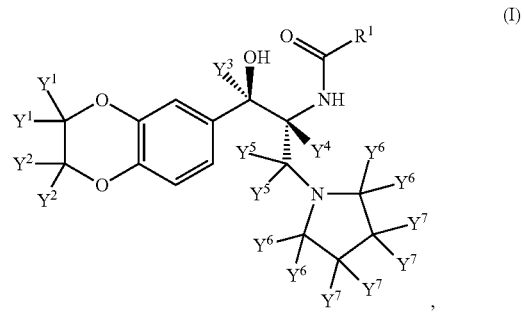

or a pharmaceutically acceptable salt thereof,
wherein
each Y$^1$ is the same and is hydrogen or deuterium;
each Y$^2$ is the same and is hydrogen or deuterium;
Y$^3$ is hydrogen or deuterium;
Y$^4$ is hydrogen or deuterium;
each Y$^5$ is the same and is hydrogen or deuterium;
each Y$^6$ is the same and is hydrogen or deuterium;
and
each Y$^7$ is the same and is hydrogen or deuterium;
R$^1$ is

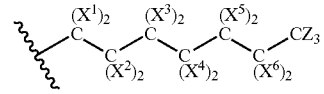

wherein
each X$^1$ is the same and is hydrogen or deuterium;
each X$^2$ is the same and is hydrogen or deuterium;
each X$^3$ is the same and is hydrogen or deuterium;
each X$^4$ is the same and is hydrogen or deuterium;
each X$^5$ is the same and is hydrogen or deuterium;
each X$^6$ is the same and is hydrogen or deuterium;
and
each Z is the same and is hydrogen or deuterium;
provided that if each Y is hydrogen and each X is hydrogen, then
each Z is deuterium.

In one embodiment, each Y$^1$ is hydrogen. In one example of this embodiment, each Y$^2$ is hydrogen. In another example of this embodiment, each Y$^2$ is deuterium. In one example of this embodiment, Y$^3$ is hydrogen. In another example of this embodiment, Y$^3$ is deuterium. In one example of this embodiment, Y$^4$ is hydrogen. In another example of this embodiment, Y$^4$ is deuterium. In one example of this embodiment, each Y$^7$ is hydrogen. In another example of this embodiment, each Y$^7$ is deuterium. In one example of this embodiment, R$^1$ is selected from —(CH$_2$)$_6$—CH$_3$, —(CH$_2$)$_6$—CD$_3$, —(CH$_2$)$_5$—CD$_2$-CD$_3$, —(CH$_2$)$_4$—(CD$_2$)$_2$-CD$_3$, —(CH$_2$)$_3$—(CD$_2$)$_3$-CD$_3$, —(CH$_2$)$_2$—(CD$_2$)$_4$-CD$_3$, —CH$_2$—(CD$_2$)$_5$-CD$_3$, and —(CD$_2$)$_6$-CD$_3$, more particularly from —(CH$_2$)$_6$—CH$_3$, —CH$_2$—(CD$_2$)$_5$-CD$_3$ and —(CD$_2$)$_6$-CD$_3$. In one example of this embodiment, each Y$^5$ is the same as each Y$^6$.

In one embodiment, each Y$^1$ is deuterium. In one example of this embodiment, each Y$^2$ is hydrogen. In another example of this embodiment, each Y$^2$ is deuterium. In one example of this embodiment, $Y^3$ is hydrogen. In another example of this embodiment, $Y^3$ is deuterium. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, each $Y^2$ is hydrogen. In one example of this embodiment, $Y^3$ is hydrogen. In another example of this embodiment, $Y^3$ is deuterium. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, each $Y^2$ is deuterium. In one example of this embodiment, $Y^3$ is hydrogen. In another example of this embodiment, $Y^3$ is deuterium. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, $Y^3$ is hydrogen. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, $Y^3$ is deuterium. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, $Y^4$ is hydrogen. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, each $Y^7$ is hydrogen. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment, each $Y^5$ is the same as each $Y^6$.

In one embodiment of a compound of Formula I, each $Y^1$ is the same as each $Y^2$, each $Y^3$ is the same as each $Y^4$, and the compound of Formula I is any one of the compounds in Table 1:

TABLE 1

Examples of Specific Compounds of Formula I

| Compound | each $Y^1$ = each $Y^2$ | each $Y^3$ = each $Y^4$ | $Y^5$ | $Y^6$ | $Y^7$ | $R^1$ |
|---|---|---|---|---|---|---|
| 101 | H | H | H | H | H | —$CH_2$—$(CD_2)_5$—$CD_3$ |
| 102 | H | H | H | H | H | —$(CD_2)_6$—$CD_3$ |
| 103 | H | H | H | H | H | —$(CH_2)_6$—$CH_3$ |
| 104 | D | H | H | H | H | —$CH_2$—$(CD_2)_5$—$CD_3$ |
| 105 | D | H | H | H | H | —$(CD_2)_6$—$CD_3$ |
| 106 | H | D | H | H | H | —$(CH_2)_6$—$CH_3$ |
| 107 | H | D | H | H | H | —$CH_2$—$(CD_2)_5$—$CD_3$ |
| 108 | H | D | H | H | H | —$(CD_2)_6$—$CD_3$ |
| 109 | H | H | H | H | D | —$(CH_2)_6$—$CH_3$ |
| 110 | H | H | H | H | D | —$CH_2$—$(CD_2)_5$—$CD_3$ |
| 111 | H | H | H | H | D | —$(CD_2)_6$—$CD_3$ |
| 112 | H | H | H | D | D | —$(CH_2)_6$—$CH_3$ |
| 113 | H | H | H | D | D | —$CH_2$—$(CD_2)_5$—$CD_3$ |
| 114 | H | H | H | D | D | —$(CD_2)_6$—$CD_3$ |
| 115 | H | H | D | D | D | —$(CH_2)_6$—$CH_3$ |
| 116 | H | H | D | D | D | —$CH_2$—$(CD_2)_5$—$CD_3$ |

TABLE 1-continued

Examples of Specific Compounds of Formula I

| Compound | each Y$^1$ = each Y$^2$ | each Y$^3$ = each Y$^4$ | Y$^5$ | Y$^6$ | Y$^7$ | R$^1$ |
|---|---|---|---|---|---|---|
| 117 | H | H | D | D | D | —(CD$_2$)$_6$—CD$_3$ |
| 180 | D | D | H | H | H | —(CH$_2$)$_6$—CH$_3$ |
| 181 | D | D | H | H | H | —CH$_2$—(CD$_2$)$_5$—CD$_3$ |
| 182 | D | D | H | H | H | —(CD$_2$)$_6$—CD$_3$ |
| 183 | D | H | H | H | D | —(CH$_2$)$_6$—CH$_3$ |
| 184 | D | H | H | H | D | —CH$_2$—(CD$_2$)$_5$—CD$_3$ |
| 185 | D | H | H | H | D | —(CD$_2$)$_6$—CD$_3$ |
| 118 | D | H | H | D | D | —(CH$_2$)$_6$—CH$_3$ |
| 119 | D | H | H | D | D | —CH$_2$—(CD$_2$)$_5$—CD$_3$ |
| 120 | D | H | H | D | D | —(CD$_2$)$_6$—CD$_3$ |
| 121 | D | H | D | D | D | —(CH$_2$)$_6$—CH$_3$ |
| 122 | D | H | D | D | D | —CH$_2$—(CD$_2$)$_5$—CD$_3$ |
| 123 | D | H | D | D | D | —(CD$_2$)$_6$—CD$_3$ |
| 124 | H | D | H | H | D | —(CH$_2$)$_6$—CH$_3$ |
| 125 | H | D | H | H | D | —CH$_2$—(CD$_2$)$_5$—CD$_3$ |
| 126 | H | D | H | H | D | —(CD$_2$)$_6$—CD$_3$ |
| 127 | H | D | H | D | D | —(CH$_2$)$_6$—CH$_3$ |
| 128 | H | D | H | D | D | —CH$_2$—(CD$_2$)$_5$—CD$_3$ |
| 129 | H | D | H | D | D | —(CD$_2$)$_6$—CD$_3$ |
| 130 | H | D | D | D | D | —(CH$_2$)$_6$—CH$_3$ |
| 131 | H | D | D | D | D | —CH$_2$—(CD$_2$)$_5$—CD$_3$ |
| 132 | H | D | D | D | D | —(CD$_2$)$_6$—CD$_3$ |
| 133 | D | D | H | H | D | —(CH$_2$)$_6$—CH$_3$ |
| 134 | D | D | H | H | D | —CH$_2$—(CD$_2$)$_5$—CD$_3$ |
| 135 | D | D | H | H | D | —(CD$_2$)$_6$—CD$_3$ |
| 136 | D | D | H | D | D | —(CH$_2$)$_6$—CH$_3$ |
| 137 | D | D | H | D | D | —CH$_2$—(CD$_2$)$_5$—CD$_3$ |
| 138 | D | D | H | D | D | —(CD$_2$)$_6$—CD$_3$ |
| 139 | D | D | D | D | D | —(CH$_2$)$_6$—CH$_3$ |
| 140 | D | D | D | D | D | —CH$_2$—(CD$_2$)$_5$—CD$_3$ |
| 141 | D | D | D | D | D | —(CD$_2$)$_6$—CD$_3$ | or a pharmaceutically acceptable salt thereof, wherein any atom not designated as deuterium is present at its natural isotopic abundance.

The present invention provides a compound of Formula Ia:

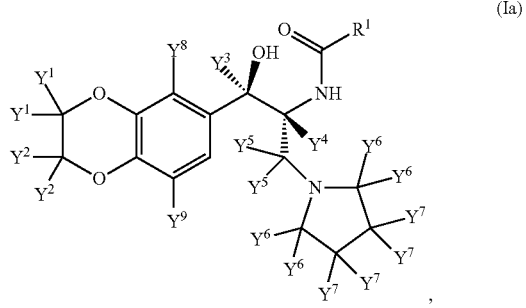

(Ia)

or a pharmaceutically acceptable salt thereof,
wherein
each Y$^1$ is the same and is hydrogen or deuterium;
each Y$^2$ is the same and is hydrogen or deuterium;
Y$^3$ is hydrogen or deuterium;
Y$^4$ is hydrogen or deuterium;
each Y$^5$ is the same and is hydrogen or deuterium;
each Y$^6$ is the same and is hydrogen or deuterium;
each Y$^7$ is the same and is hydrogen or deuterium;
Y$^8$ is hydrogen or deuterium;
Y$^9$ is hydrogen or deuterium;
and
Y$^{10}$ is hydrogen or deuterium;
R$^1$ is

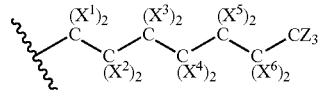

wherein
each X$^1$ is the same and is hydrogen or deuterium;
each X$^2$ is the same and is hydrogen or deuterium;
each X$^3$ is the same and is hydrogen or deuterium;
each X$^4$ is the same and is hydrogen or deuterium;
each X$^5$ is the same and is hydrogen or deuterium;
each X$^6$ is the same and is hydrogen or deuterium;
and
each Z is the same and is hydrogen or deuterium;
provided that one of Y$^3$ and Y$^4$ is hydrogen and the other of Y$^3$ and Y$^4$ is deuterium.

In one embodiment of a compound of Formula Ia, each Y$^1$ is hydrogen. In one example of this embodiment, each Y$^2$ is hydrogen. In another example of this embodiment, each Y$^2$ is deuterium. In one example of this embodiment, Y$^3$ is hydrogen and Y$^4$ is deuterium. In another example of this embodiment, Y$^3$ is deuterium and Y$^4$ is hydrogen. In one example of this embodiment, each Y$^5$ is hydrogen. In another example of this embodiment, each Y$^5$ is deuterium. In one example of this embodiment, R$^1$ is selected from —(CH$_2$)$_6$—CH$_3$, —(CH$_2$)$_6$—CD$_3$, —(CH$_2$)$_5$—CD$_2$-CD$_3$, —(CH$_2$)$_4$—(CD$_2$)$_2$-CD$_3$, —(CH$_2$)$_3$—(CD$_2$)$_3$-CD$_3$, —(CH$_2$)$_2$—(CD$_2$)$_4$-CD$_3$, —CH$_2$—(CD$_2$)$_5$-CD$_3$, and —(CD$_2$)$_6$-CD$_3$, more particularly from —(CH$_2$)$_6$—CD$_3$, —(CH$_2$)$_5$—CD$_2$-CD$_3$, —(CH$_2$)$_4$—(CD$_2$)$_2$-CD$_3$, —(CH$_2$)$_3$—(CD$_2$)$_3$-CD$_3$, —(CH$_2$)$_2$—(CD$_2$)$_4$-CD$_3$, —CH$_2$—(CD$_2$)$_5$-CD$_3$, and —(CD$_2$)$_6$-CD$_3$. In one example R$^1$ is —(CD$_2$)$_6$-CD$_3$. In one example of this embodiment, each Y$^6$ is the same as each Y$^7$.

In one embodiment of a compound of Formula Ia, each Y$^1$ is deuterium. In one example of this embodiment, each Y$^2$ is hydrogen. In another example of this embodiment, each Y$^2$ is deuterium. In one example of this embodiment, Y$^3$ is hydrogen and Y$^4$ is deuterium. In another example of this embodiment, Y$^3$ is deuterium and Y$^4$ is hydrogen. In one example of this embodiment, each Y$^5$ is hydrogen. In another example of this embodiment, each Y$^5$ is deuterium. In one example of this embodiment, R$^1$ is selected from —(CH$_2$)$_6$—CH$_3$, —(CH$_2$)$_6$—CD$_3$, —(CH$_2$)$_5$—CD$_2$-CD$_3$, —(CH$_2$)$_4$—(CD$_2$)$_2$-CD$_3$, —(CH$_2$)$_3$—(CD$_2$)$_3$-CD$_3$, —(CH$_2$)$_2$—(CD$_2$)$_4$-CD$_3$, —CH$_2$—(CD$_2$)$_5$-CD$_3$, and —(CD$_2$)$_6$-CD$_3$, more particularly from —(CH$_2$)$_6$—CD$_3$, —(CH$_2$)$_5$—CD$_2$-CD$_3$, —(CH$_2$)$_4$—(CD$_2$)$_2$-CD$_3$, —(CH$_2$)$_3$—(CD$_2$)$_3$-CD$_3$, —(CH$_2$)$_2$—(CD$_2$)$_4$-CD$_3$, —CH$_2$—(CD$_2$)$_5$-CD$_3$, and —(CD$_2$)$_6$-CD$_3$. In one example R$^1$ is —(CD$_2$)$_6$-CD$_3$. In one example of this embodiment, each Y$^6$ is the same as each V.

In certain embodiments of a compound of Formula Ia, each of Y$^8$, Y$^9$ and Y$^{10}$ is hydrogen. In certain other embodiments of a compound of Formula Ia, each of Y$^8$, Y$^9$ and Y$^{10}$ is deuterium. In certain embodiments of a compound of Formula Ia, each Y$^5$ is deuterium and each Y$^6$ is hydrogen. In certain embodiments of a compound of Formula Ia, each of Y$^1$, Y$^2$, Y$^5$, Y$^6$, and Y$^7$ are as in any of the embodiments described for a compound of Formula I.

In one embodiment of a Compound of Formula Ia, $Y^3$ is deuterium and $Y^4$ is hydrogen. In one example of this embodiment, each $Y^5$ is hydrogen. In another example of this embodiment, each $Y^5$ is deuterium. In one example of this embodiment, each $Y^5$ is deuterium, and each $Y^6$ is the same as each $Y^7$. In one example of this embodiment, each $Y^5$ is deuterium, and each $Y^6$ and each $Y^7$ is deuterium. In one example of this embodiment, each $Y^5$ is hydrogen, and each $Y^6$ and each $Y^7$ is deuterium. In one example of this embodiment, each $Y^5$ is deuterium, each $Y^6$ and each $Y^7$ is deuterium, and each of $Y^8$, $Y^9$ and $Y^{10}$ is hydrogen. In one example of this embodiment, each $Y^5$ is hydrogen, each $Y^6$ and each $Y^7$ is deuterium, and each of $Y^8$, $Y^9$ and $Y^{10}$ is hydrogen.

In one embodiment of a Compound of Formula Ia, $Y^3$ is hydrogen and $Y^4$ is deuterium. In one example of this embodiment, each $Y^5$ is hydrogen. In another example of this embodiment, each $Y^5$ is deuterium. In one example of this embodiment, each $Y^5$ is deuterium, and each $Y^6$ is the same as each $Y^7$. In one example of this embodiment, each $Y^5$ is deuterium, and each $Y^6$ and each $Y^7$ is deuterium. In one example of this embodiment, each $Y^5$ is hydrogen, and each $Y^6$ and each $Y^7$ is deuterium. In one example of this embodiment, each $Y^5$ is deuterium, each $Y^6$ and each $Y^7$ is deuterium, and each of $Y^8$, $Y^9$ and $Y^{10}$ is hydrogen. In one example of this embodiment, each $Y^5$ is hydrogen, each $Y^6$ and each $Y^7$ is deuterium, and each of $Y^8$, $Y^9$ and $Y^{10}$ is hydrogen.

In one embodiment of a compound of Formula Ia, each $Y^1$ is the same as each $Y^2$ and the compound of Formula Ia is any one of the compounds in Table 2:

TABLE 2

Examples of Specific Compounds of Formula Ia

| Compound | each $Y^1$ = each $Y^2$ | $Y^3$ | $Y^4$ | $Y^5$ | $Y^6$ | $Y^7$ | $R^1$ |
|---|---|---|---|---|---|---|---|
| 142 | H | D | H | H | H | H | —(CH$_2$)$_6$—CH$_3$ |
| 143 | H | D | H | H | D | D | —(CH$_2$)$_6$—CH$_3$ |
| 144 | H | D | H | H | H | H | —(CD$_2$)$_6$—CD$_3$ |
| 145 | D | D | H | H | H | H | —(CD$_2$)$_6$—CD$_3$ |
| 146 | H | D | H | H | H | D | —(CD$_2$)$_6$—CD$_3$ |
| 147 | H | D | H | H | D | D | —(CD$_2$)$_6$—CD$_3$ |
| 158 | H | D | H | D | D | D | —(CD$_2$)$_6$—CD$_3$ |
| 159 | D | D | H | H | H | D | —(CD$_2$)$_6$—CD$_3$ |
| 150 | D | D | H | H | D | D | —(CD$_2$)$_6$—CD$_3$ |
| 151 | D | D | H | D | D | D | —(CD$_2$)$_6$—CD$_3$ |
| 152 | H | D | H | D | H | H | —(CD$_2$)$_6$—CD$_3$ |
| 153 | H | D | H | D | D | H | —(CD$_2$)$_6$—CD$_3$ |
| 154 | H | D | H | D | D | H | —(CD$_2$)$_6$—CD$_3$ |
| 155 | D | D | H | D | D | H | —(CD$_2$)$_6$—CD$_3$ |
| 156 | H | H | D | H | H | H | —(CH$_2$)$_6$—CH$_3$ |
| 157 | H | H | D | H | D | D | —(CH$_2$)$_6$—CH$_3$ |
| 158 | H | H | D | H | H | H | —(CD$_2$)$_6$—CD$_3$ |
| 159 | D | H | D | H | H | H | —(CD$_2$)$_6$—CD$_3$ |
| 160 | H | H | D | H | H | D | —(CD$_2$)$_6$—CD$_3$ |
| 161 | H | H | D | H | D | D | —(CD$_2$)$_6$—CD$_3$ |
| 162 | H | H | D | D | D | D | —(CD$_2$)$_6$—CD$_3$ |
| 163 | D | H | D | H | H | D | —(CD$_2$)$_6$—CD$_3$ |
| 164 | D | H | D | H | D | D | —(CD$_2$)$_6$—CD$_3$ |
| 165 | D | H | D | D | D | D | —(CD$_2$)$_6$—CD$_3$ |
| 166 | H | H | D | D | H | H | —(CD$_2$)$_6$—CD$_3$ |
| 167 | H | H | D | D | D | H | —(CD$_2$)$_6$—CD$_3$ |
| 168 | D | H | D | D | H | H | —(CD$_2$)$_6$—CD$_3$ |
| 169 | D | H | D | D | D | H | —(CD$_2$)$_6$—CD$_3$ | or a pharmaceutically acceptable salt thereof, wherein any atom not designated as deuterium is present at its natural isotopic abundance.

The present invention provides a compound of Formula Ib:

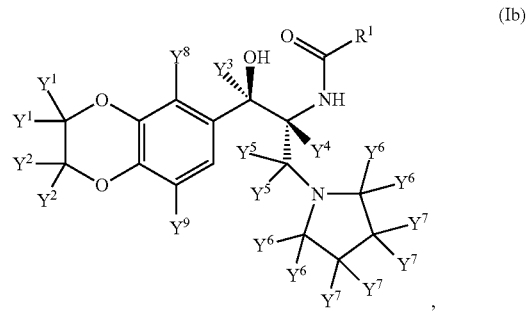

or a pharmaceutically acceptable salt thereof,
wherein
each $Y^1$ is the same and is hydrogen or deuterium;
each $Y^2$ is the same and is hydrogen or deuterium;
$Y^3$ is hydrogen or deuterium;
$Y^4$ is hydrogen or deuterium;
each $Y^5$ is deuterium;
each $Y^6$ is hydrogen;
each $Y^7$ is the same and is hydrogen or deuterium;
$Y^8$ is hydrogen or deuterium;
$Y^9$ is hydrogen or deuterium;
and
$Y^{10}$ is hydrogen or deuterium;
$R^1$ is

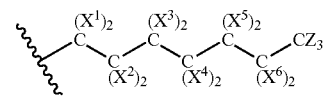

wherein
each $X^1$ is the same and is hydrogen or deuterium;
each $X^2$ is the same and is hydrogen or deuterium;
each $X^3$ is the same and is hydrogen or deuterium;
each $X^4$ is the same and is hydrogen or deuterium;
each $X^5$ is the same and is hydrogen or deuterium;
each $X^6$ is the same and is hydrogen or deuterium;
and
each Z is the same and is hydrogen or deuterium.

In one embodiment, each $Y^1$ is hydrogen. In one example of this embodiment, each $Y^2$ is hydrogen. In another example of this embodiment, each $Y^2$ is deuterium. In one example of this embodiment, $Y^3$ is hydrogen. In another example of this embodiment, $Y^3$ is deuterium. In one example of this embodiment, $Y^4$ is hydrogen. In another example of this embodiment, $Y^4$ is deuterium. In one example of this embodiment, each $Y^7$ is hydrogen. In one example of this embodiment, $R^1$ is selected from —(CH$_2$)$_6$—CH$_3$, —(CH$_2$)$_6$—CD$_3$, —(CH$_2$)$_5$—CD$_2$-CD$_3$, —(CH$_2$)$_4$—(CD$_2$)$_2$-CD$_3$, —(CH$_2$)$_3$—(CD$_2$)$_3$-CD$_3$, —(CH$_2$)$_2$—(CD$_2$)$_4$-CD$_3$, —CH$_2$—(CD$_2$)$_5$-CD$_3$, and —(CD$_2$)$_6$-CD$_3$, more particularly from —(CH$_2$)$_6$—CD$_3$, —(CH$_2$)$_5$—CD$_2$-CD$_3$, —(CH$_2$)$_4$—(CD$_2$)$_2$-CD$_3$, —(CH$_2$)$_3$—(CD$_2$)$_3$-CD$_3$, —(CH$_2$)$_2$—(CD$_2$)$_4$-CD$_3$, —CH$_2$—(CD$_2$)$_5$-CD$_3$, and —(CD$_2$)$_6$-CD$_3$. In one example $R^1$ is —(CD$_2$)$_6$-CD$_3$.

In one embodiment, each $Y^1$ is hydrogen. In one example of this embodiment, each $Y^2$ is hydrogen. In another example of this embodiment, each $Y^2$ is deuterium. In one example of this embodiment, $Y^3$ is hydrogen. In another example of this embodiment, $Y^3$ is deuterium. In one example of this embodiment, $Y^4$ is hydrogen. In another example of this embodiment, $Y^4$ is deuterium. In one embodiment, one of $Y^3$ and $Y^4$ is hydrogen and the other of $Y^3$ and $Y^4$ is deuterium. In one example of this embodiment, each $Y^7$ is hydrogen. In one example of this embodiment, $R^1$ is selected from —$(CH_2)_6$—$CH_3$, —$(CH_2)_6$—$CD_3$, —$(CH_2)_5$ —$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$. In one example $R^1$ is —$(CD_2)_6$-$CD_3$.

In certain embodiments of a compound of Formula Ib, each of $Y^8$, $Y^9$ and $Y^{10}$ is hydrogen. In certain other embodiments of a compound of Formula Ib, each of $Y^8$, $Y^9$ and $Y^{10}$ is deuterium. In certain embodiments of a compound of Formula Ia, each of $Y^1$, $Y^2$, $Y^3$, $Y^4$, and $Y^7$ are as in any of the embodiments described for a compound of Formula I.

In one embodiment of a compound of Formula Ib, each $Y^1$ is the same as each $Y^2$, each $Y^3$ is the same as each $Y^4$, $Y^8$, $Y^9$, $Y^{10}$ are each hydrogen, and the compound of Formula Ib is any one of the compounds in Table 3:

TABLE 3

Examples of Specific Compounds of Formula Ib

| Compound | each $Y^1$ = each $Y^2$ | each $Y^3$ = each $Y^4$ | $Y^7$ | $R^1$ |
|---|---|---|---|---|
| 170 | H | H | H | —$(CH_2)_6$—$CH_3$ |
| 171 | H | H | H | —$(CD_2)_6$—$CD_3$ |
| 172 | D | H | H | —$(CD_2)_6$—$CD_3$ |
| 173 | H | H | D | —$(CD_2)_6$—$CD_3$ |
| 174 | D | H | D | —$(CD_2)_6$—$CD_3$ |
| 175 | H | D | H | —$(CH_2)_6$—$CH_3$ |
| 176 | H | D | H | —$(CD_2)_6$—$CD_3$ |
| 177 | D | D | H | —$(CD_2)_6$—$CD_3$ |
| 178 | H | D | D | —$(CD_2)_6$—$CD_3$ |
| 179 | D | D | D | —$(CD_2)_6$—$CD_3$ | or a pharmaceutically acceptable salt thereof, wherein any atom not designated as deuterium is present at its natural isotopic abundance.

The present invention provides a compound of Formula Ic:

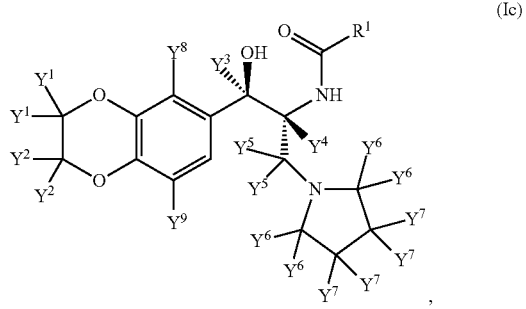

(Ic)

or a pharmaceutically acceptable salt thereof,
wherein
each $Y^1$ is the same and is hydrogen or deuterium;
each $Y^2$ is the same and is hydrogen or deuterium;
$Y^3$ is hydrogen or deuterium;
$Y^4$ is hydrogen or deuterium;
each $Y^5$ is the same and is hydrogen or deuterium;
each $Y^6$ is the same and is hydrogen or deuterium;
each $Y^7$ is the same and is hydrogen or deuterium;
$Y^8$ is hydrogen or deuterium;
$Y^9$ is is hydrogen or deuterium;
and
$Y^{10}$ is hydrogen or deuterium;
$R^1$ is

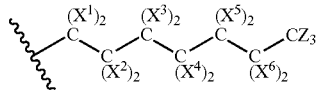

wherein
each $X^1$ is the same and is hydrogen or deuterium;
each $X^2$ is the same and is hydrogen or deuterium;
each $X^3$ is the same and is hydrogen or deuterium;
each $X^4$ is the same and is hydrogen or deuterium;
each $X^5$ is the same and is hydrogen or deuterium;
each $X^6$ is the same and is hydrogen or deuterium;
and
each Z is the same and is hydrogen or deuterium;
provided that at least one of $Y^8$, $Y^9$ and $Y^{10}$ is deuterium.

In certain embodiments of a compound of Formula Ic, each of $Y^8$, $Y^9$ and $Y^{10}$ is deuterium. In certain embodiments of a compound of Formula Ic, one of $Y^3$ and $Y^4$ is hydrogen and the other of $Y^3$ and $Y^4$ is deuterium. In certain embodiments of a compound of Formula Ic, each $Y^5$ is deuterium and each $Y^6$ is hydrogen.

In one embodiment of a compound of Formula Ic, each $Y^1$ is hydrogen. In one example of this embodiment, each $Y^2$ is hydrogen. In another example of this embodiment, each $Y^2$ is deuterium. In one example of this embodiment, $Y^3$ is hydrogen. In another example of this embodiment, $Y^3$ is deuterium. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$ —$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, each $Y^1$ is deuterium. In one example of this embodiment, each $Y^2$ is hydrogen. In another example of this embodiment, each $Y^2$ is deuterium. In one example of this embodiment, $Y^3$ is hydrogen. In another example of this embodiment, $Y^3$ is deuterium. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$ —$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, each $Y^2$ is hydrogen. In one example of this embodiment, $Y^3$ is hydrogen. In another example of this embodiment, $Y^3$ is deuterium. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, each $Y^2$ is deuterium. In one example of this embodiment, $Y^3$ is hydrogen. In another example of this embodiment, $Y^3$ is deuterium. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, $Y^3$ is hydrogen. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, $Y^3$ is deuterium. In one example of this embodiment, $Y^4$ is hydrogen. In another example of this embodiment, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, $Y^4$ is hydrogen. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, $Y^4$ is deuterium. In one example of this embodiment, each $Y^7$ is hydrogen. In another example of this embodiment, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, each $Y^7$ is hydrogen. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, each $Y^7$ is deuterium. In one example of this embodiment, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, $R^1$ is selected from —$(CH_2)_6$—$CH_3$, —$(CH_2)_6$—$CD_3$, —$(CH_2)_5$—$CD_2$-$CD_3$, —$(CH_2)_4$—$(CD_2)_2$-$CD_3$, —$(CH_2)_3$—$(CD_2)_3$-$CD_3$, —$(CH_2)_2$—$(CD_2)_4$-$CD_3$, —$CH_2$—$(CD_2)_5$-$CD_3$, and —$(CD_2)_6$-$CD_3$, more particularly from —$(CH_2)_6$—$CH_3$, —$CH_2$—$(CD_2)_5$-$CD_3$ and —$(CD_2)_6$-$CD_3$. In one example of this embodiment, each $Y^5$ is the same as each $Y^6$.

In one embodiment of a compound of Formula Ic, each $Y^5$ is the same as each $Y^6$.

In another set of embodiments, any atom not designated as deuterium in any of the embodiments set forth above is present at its natural isotopic abundance.

The synthesis of compounds of Formula I, Ia, Ib and Ic can be readily achieved by synthetic chemists of ordinary skill. Exemplary deuterated compounds may be prepared using appropriately deuterated reagents and solvents in a manner analogous to that described in U.S. Pat. No. 8,138,353 utilizing suitable deuterated intermediates and reagents.

Exemplary Synthesis

A convenient method for synthesizing compounds of Formula I is depicted in Scheme 1.

Scheme 1: Method for Synthesizing Compounds of Formula I

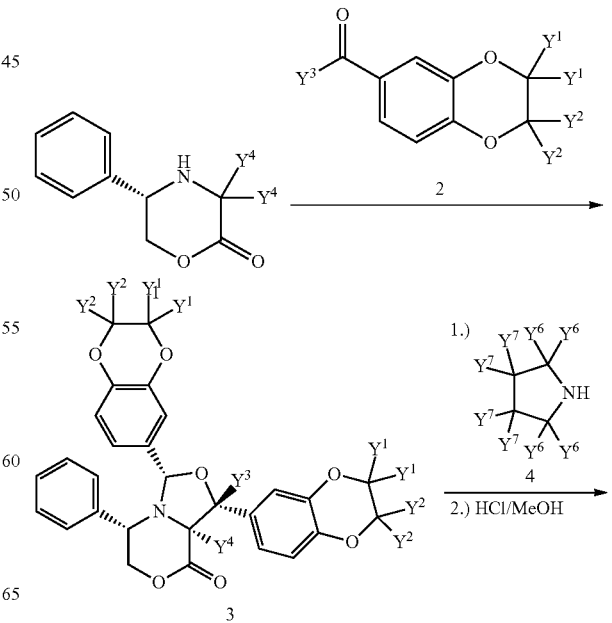

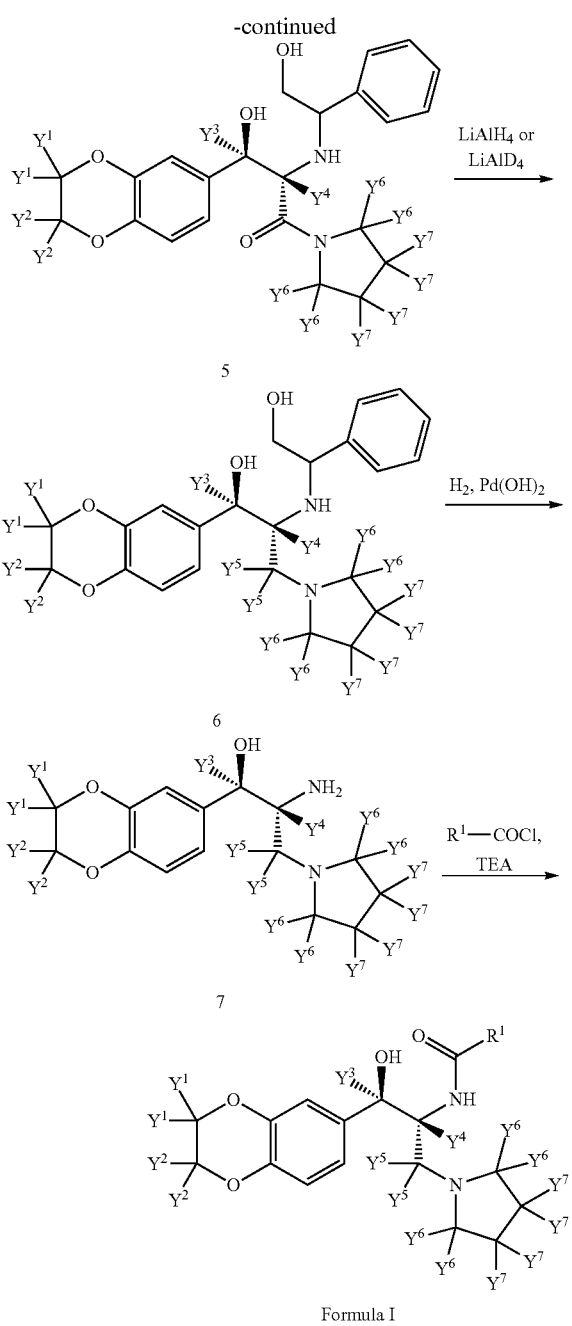

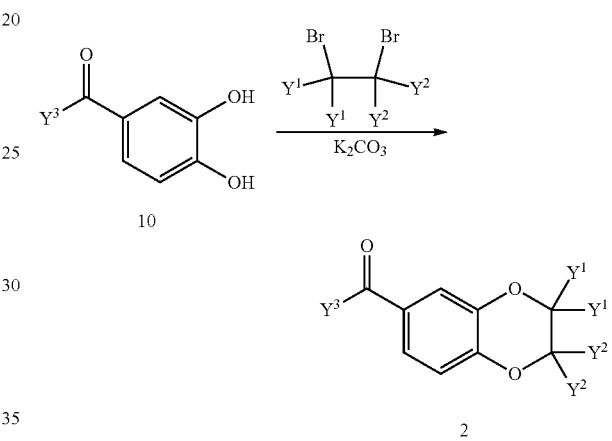

Scheme 2: Method of Synthesizing Compound 2

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. For example, both ethylene glycol and 1,1,2,2-tetradeutero ethylene glycol are commercially available and may be used in the preparation of 2 for use in Scheme 1. As another example, pyrrolidine 4 (4a; $Y^6$=D and $Y^7$=H) is commercially available from CDN Isotopes; 4b: $Y^6$=H and $Y^7$=D has been previously prepared and described in international patent application WO 2010132810 A1; 4c: $Y^6$=D and $Y^7$=D is commercially available from CDN Isotopes; 4d: $Y^6$=H and $Y^7$=H is commercially available from Sigma-Aldrich). Certain intermediates can be used with or without purification (e.g., filtration, distillation, sublimation, crystallization, trituration, solid phase extraction, and chromatography).

A compound of Formula Ia, Ib, or Ic may be prepared in the same manner as shown in Scheme 1 for a compound of Formula I. For a compound of Formula Ia, Ib, or Ic, wherein at least one of $Y^8$, $Y^9$ and $Y^{10}$ is deuterium, the compound may be prepared using a deuterated pyrocatechol to prepare intermediate 10, as described below or by invoking standard synthetic protocols known in the art for introducing isotopic atoms to a chemical structure for use in preparing intermediate 2.

A method for synthesizing compound 2 for use in Scheme 1, in a manner analogous to that reported in Li, D-D et al., Bioorg. Med. Chem. Lett., 2012, 22(18), p. 5870-5875, is depicted in Scheme 2.

10a (i.e., 10 where $Y^3$ is hydrogen) is a known compound. 10b (i.e., 10 where $Y^3$ is deuterium) may be prepared in a manner analogous to 10a, for example from pyrocatechol, as described by Ravichandran, R., Journal of Molecular Catalysis A: Chemical, 130(3), L205-L207; 1998, by replacing chloroform with $CDCl_3$. Deuterated pyrocatechol is commercially available as 1,2-benzene-3,4,5,6-$d_4$-diol, and as 1,2-benzene-3,4,5,6-$d_4$-diol-$d_2$ and may be used in the preparation of intermediate 2. As stated above, both ethylene glycol and 1,1,2,2-tetradeutero ethylene glycol are commercially available and may be used in the preparation of 2 as outlined above.

The methods described in the foregoing patent application may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, Comprehensive Organic Transformations, VCH Publishers (1989); Greene T W et al., Protective Groups in Organic Synthesis, 3$^{rd}$ Ed., John Wiley and Sons (1999); Fieser L et al., Fieser and Fieser's Reagents for Organic Synthesis, John Wiley and Sons (1994); and Paquette L, ed., Encyclopedia of Reagents for Organic Synthesis, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula I, Ia, Ib or Ic (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as eliglustat. Such agents include those indicated as being useful in combination with eliglustat.

Preferably, the second therapeutic agent is an agent useful in the treatment of a condition selected from Tay-Sach's disease, Gaucher's disease, and Fabry's disease.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N. Y., 1970, 537.

In one embodiment, an effective amount of a compound of this invention can range from about 10 mg to 1000 mg per day, such as from about 15 to 600 mg per day, such as from about 25 to 450 mg per day, such as from about 50 mg to 250 mg per day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

Methods of Treatment

In another embodiment, the invention provides a method of inhibiting UDP-glucose: N-acyl-sphingosine glucosyltransferase in a cell, comprising contacting a cell with a compound of Formula I, Ia, Ib or Ic herein.

According to another embodiment, the invention provides a method of treating a disease or condition that may be treated by eliglustat, comprising administering to a subject an effective amount of a compound or a composition of this invention. In one embodiment, the condition is a glycosphingolipidosis disorder. In one embodiment, the glycosphingolipidosis disorder is selected from Tay-Sach's disease, Gaucher's disease, and Fabry's disease. In one embodiment, the condition is selected from diabetes, fatty liver disease, polycystic kidney disease, and lupus.

Identifying a subject in need of such treatment can be in the judgment of a subject or a health care professional and can be subjective (e.g. opinion) or objective (e.g. measurable by a test or diagnostic method). In one embodiment the subject is a patient.

In another embodiment, any of the above methods of treatment comprises the further step of co-administering to the subject in need thereof one or more second therapeutic agents. The choice of second therapeutic agent may be made from any second therapeutic agent known to be useful for co-administration with eliglustat. The choice of second therapeutic agent is also dependent upon the particular disease or condition to be treated. Examples of second therapeutic agents that may be employed in the methods of this invention are therapeutics useful in treating myelofibrosis.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I, Ia, Ib, or Ic alone or together with one or more of the above-described second therapeutic agents in the manufacture of a medicament, either as a single composition or as separate dosage forms, for treatment in a subject of a disease, disorder or symptom set forth above. Another aspect of the invention is a compound of Formula I, Ia, Ib, or Ic for use in the treatment in a subject of a disease, disorder or symptom thereof delineated herein.

EXAMPLES

Example 1

N-((1R,2R)-1-(2,3-Dihydrobenzo[b][1,4]dioxin-6-yl)-1-hydroxy-3-(pyrrolidin-1-yl)propan-2-yl)-octan-d15-amide hemi-L-tartaric acid salt (Compound 102•tartrate salt)

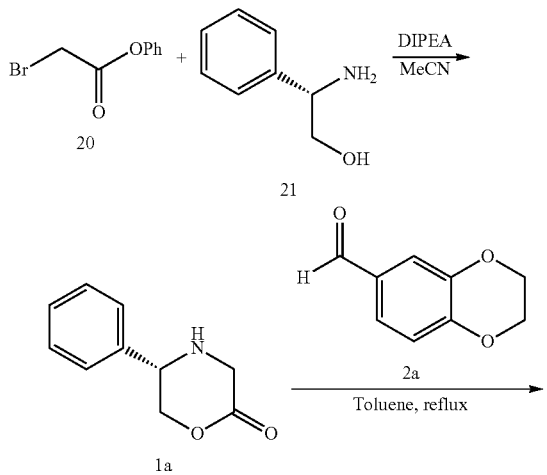

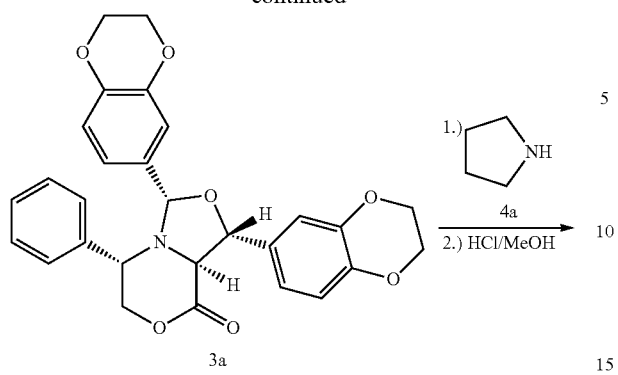

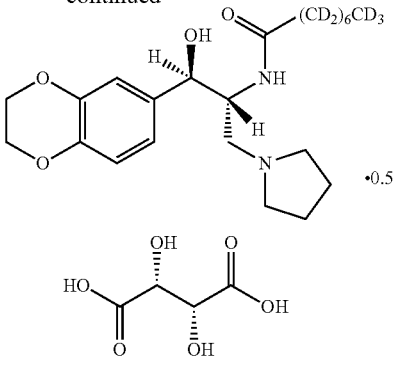

Compound 102. tartrate salt

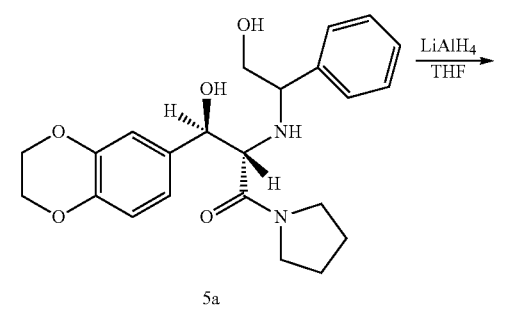

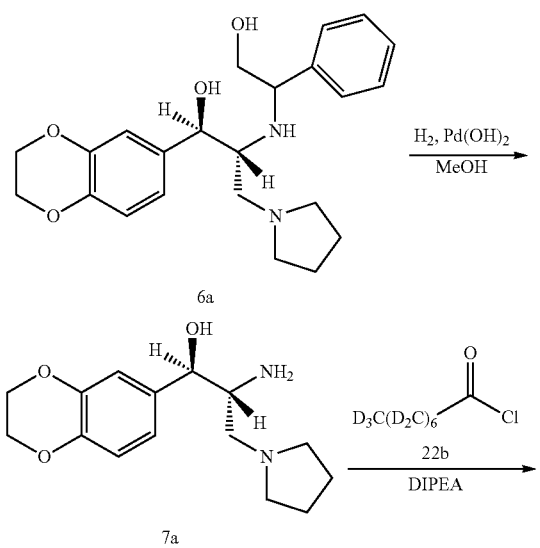

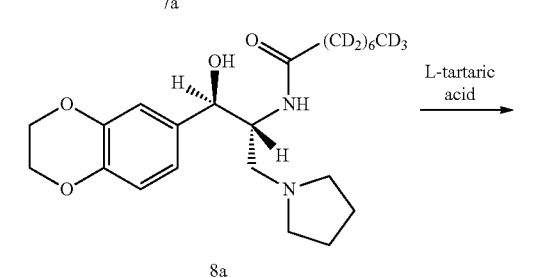

Step 1. (S)-5-Phenylmorpholin-2-one (1a)

To a solution of phenyl bromoacetate (20) (25.9 g, 120.4 mmol) in acetonitrile (90 mL) was added dropwise a solution of (S)-(+)-2-amino-2-phenylethan-1-ol (21) (15.0 g, 109.5 mmol), and diisopropylethylamine (47.7 mL, 273.8 mmol) in acetonitrile (360 mL) at room temperature over 2 hours. The reaction mixture was stirred at room temperature for 16 hours, concentrated under reduced pressure at <20° C. and purified by silica gel chromatography, eluting with 0 to 100% ethyl acetate in heptanes to afford (1a) (13.3 g, 69% yield) as a beige oil, which was dissolved in benzene (66 mL) and stored at low temperature. (Caution! (1a) is unstable at elevated temperature and on silica gel for extended time period, and so, a temperature of <20-25° C. was maintained when concentrating reaction mixture and column fractions).

Step 2. (1R,3S,5S,8aS)-1,3-Bis(2,3-dihydrobenzo[b][1,4]dioxin-6-yl)-5-phenyltetrahydro-3H,8H-oxazolo[4,3-c][1,4]oxazin-8-one (3a)

To a solution of 2,3-dihydro-1,4-benzodioxine-6-carbaldehyde (2a) (22.3 g, 136 mmol) in anhydrous toluene (200 mL) was added 1.13M solution of (1a) in benzene (40.0 mL, 45.2 mmol). The reaction flask was equipped with a Soxhlet extractor filled with activated 4 Å molecular sieves (60 g), and refluxed vigorously for 3 days, cooled to room temperature and a solution of sodium metabisulfite (43 g) in water (120 mL) was added. After stirring for 1 hour, a white solid was filtered and washed with ethyl acetate. The filtrate was placed in a separatory funnel and the separated organic layer was washed with water (200 mL), saturated sodium chloride (150 mL), dried over sodium sulfate, filtered and concentrated under reduced pressure. The residue was dried in vacuo to give a brown solid (17.1 g) which was triturated with diethyl ether (300 mL) overnight, filtered and washed with diethyl ether (100 mL) to give a yellow solid (9.5 g) which was purified on an AnaLogix automated chromatography system, eluting with a gradient of 10 to 50% ethyl acetate in heptanes. Product fractions were pooled and evaporated in vacuo to afford 3a (6.06 g, 28% yield) as a yellow solid.

Step 3. (2S,3R)-3-(2,3-Dihydrobenzo[b][1,4]dioxin-6-yl)-3-hydroxy-2-((2-hydroxy-1-phenylethyl)amino)-1-(pyrrolidin-1-yl)propan-1-one (5a)

To a solution of 3a (6.04 g, 12.4 mmol) in dichloromethane (60 mL) was added pyrrolidine 4a (4.2 mL, 50 mmol).

The mixture was stirred at room temperature for 64 hours, concentrated under reduced pressure and the residue was dissolved in methanol (20 mL) and concentrated under reduced pressure (process repeated 2x). The resulting yellow oil was dissolved in methanol (55 mL), 1M aqueous HCl (55 mL) and refluxed for 5 hours. The reaction mixture was cooled to room temperature, concentrated under reduced pressure, and ethyl acetate (130 mL) was added and stirred for 30 minutes. The layers were separated and the organic layer was extracted with 1M HCl (120 mL). The combined aqueous layers were washed twice with ethyl acetate, adjusted to pH 5 with 1M NaOH, then to pH 8 with saturated sodium bicarbonate solution. Finally, the aqueous mixture was extracted with ethyl acetate (3×150 mL) and the combined organic layers were washed with saturated sodium chloride (75 mL), dried over sodium sulfate, filtered and concentrated under reduced pressure to furnish 5a (3.82 g, 75% yield) as a yellowish foam which was taken directly to the next step without further purification.

Step 4. (1R,2R)-1-(2,3-Dihydrobenzo[b][1,4]dioxin-6-yl)-2-(2-hydroxy-1-phenylethyl)amino)-3-(pyrrolidin-1-yl)propan-1-ol (6a)

To a solution of 5a (1.97 g, 4.77 mmol) in anhydrous THF (25 mL) at 0° C. was added a 1.0M solution of lithium aluminum hydride in THF (11.9 mL, 11.9 mmol). The reaction mixture was stirred at room temperature for 20 hours. The mixture was cooled to 0° C. and additional 1.0M lithium aluminum hydride solution in THF (4.0 mL, 0.84 mmol) was added. The mixture was further stirred at room temperature for 20 hours, cooled to 0° C., quenched by dropwise addition of 10% NaOH, diluted with water (30 mL) and filtered. The filtrate was extracted with ethyl acetate (3×60 mL) and the combined organic layers were washed with saturated sodium chloride (40 mL), dried over sodium sulfate, filtered and concentrated under reduced pressure to afford 6a (1.52 g, 80% yield) as a yellow foam, which was taken directly to the next step without further purification.

Step 5. (1R,2R)-2-Amino-1-(2,3-dihydrobenzo[b][1,4]dioxin-6-yl)-3-(pyrrolidin-1-yl)propan-1-ol (7a)

To a solution of 6a (1.52 g, 3.81 mmol) in methanol (40 mL) was added palladium hydroxide on carbon (200 mg), trifluoroacetic acid (5 mL) and water (4 mL) and the mixture was stirred under hydrogen (50 psi) at room temperature for 16 hours. Hydrogen was evacuated and replaced with nitrogen and the resulting mixture was filtered through a bed of celite, washed with methanol (40 mL) and the combined filtrate concentrated under reduced pressure. Water (40 mL) was added and the aqueous solution was extracted with ethyl acetate (3×25 mL). The aqueous phase was adjusted to pH 12 with a 24% NaOH, and was extracted with dichloromethane (3×40 mL). The combined organic layers were dried over sodium sulfate, filtered and concentrated under reduced pressure. Chloroform was added (20 mL) and the solution was concentrated under reduced pressure. The residue was dried in vacuo at room temperature overnight to afford 7a (0.55 g, 52% yield) as a yellowish foam, which was taken directly to the next step without further purification.

Preparation of Octanoyl chloride-d15 (22b)

Octanoic-d15-acid (0.63 g, 3.95 mmol, CDN Isotopes, 98.2 atom % D) was stirred in thionyl chloride (2.4 mL, 32.9 mmol) in a teflon capped vial overnight. The mixture was concentrated under reduced pressure at room temperature.

Toluene (5 mL) was added and the mixture was concentrated under reduced pressure (process repeated 3x). The residue was dried in a vacuo at room temperature for 2 hours to afford 22b (0.54 g, 77% yield) as a colorless liquid.

Step 6. N-(1R,2R)-1-(2,3-Dihydrobenzo[b][1,4]dioxin-6-yl)-1-hydroxy-3-(pyrrolidin-1-yl)propan-2-yl)-octan-d15-amide (8a)

To a solution of 7a (0.55 g, 1.97 mmol) in dichloromethane (10 mL) at 0° C. was added diisopropylethylamine (0.33 mL, 1.87 mmol), followed by a dropwise addition of a solution of 22b (0.28 g, 1.58 mmol) in dichloromethane (5 mL). The mixture was stirred at 0° C. for 3 hours and at room temperature for 1 hour, diluted with 10% NaOH (15 mL) and the biphasic mixture was stirred for 1 hour. The layers were separated and the aqueous layer was extracted with dichloromethane (3×25 mL). The combined organic layers were dried over sodium sulfate, filtered, concentrated under reduced pressure and the residue was purified by reverse phase chromatography on an AnaLogix automated chromatography system, eluting with a gradient of 0 to 50% acetonitrile in water. Product fractions were pooled and evaporated in vacuo, to afford 8a (0.22 g, 33% yield) as a colorless oil.

Step 7. N-((1R,2R120465-01706•tartrate salt)

L-tartaric acid (39.7 mg, 0.26 mmol) was dissolved in acetone (1 mL) at 55° C. The solution was added to a solution of 8a (222 mg, 0.53 mmol) in acetone (3 mL) at room temperature and the mixture was stirred at room temperature for 30 minutes, a white precipitate resulted which was heated to 55° C. for 10 minutes and then stirred at room temperature for 2 hours. The solid was filtered, washed with cold acetone (3 mL) and dried in vacuo at room temperature to afford 102•tartrate salt (234 mg, 89% yield) as a white solid. 1H NMR (DMSO-$d_6$, 300 MHz) δ 7.49-7.46 (d, J=9.1 Hz, 1H), 6.78-6.73 (m, 3H), −4.68-4.67 (m, 1H), 4.19 (s, 4H), 4.09-4.07 (m, 1H), 3.94 (s, 1H), 2.89 (m, 1H), 2.74 (m, 4H), 2.5 (m, 1H), 1.75 (m, 4H); MS (ESI) 420.2 [(M+H)$^+$].

Example 2

N-(1R,2R)-1-(2,3-Dihydrobenzo[b][1,4]dioxin-6-yl)-1-hydroxy-3-(pyrrolidin-1-yl-d8)propan-2-yl)octanamide hemi-L-tartaric acid salt (Compound 112•tartrate salt)

Scheme 2a. Preparation of Compound 112•tartrate salt

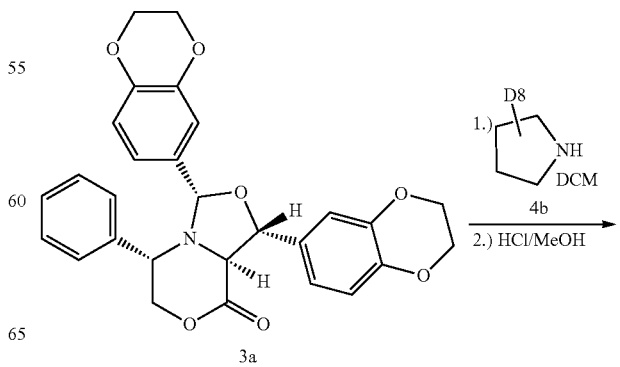

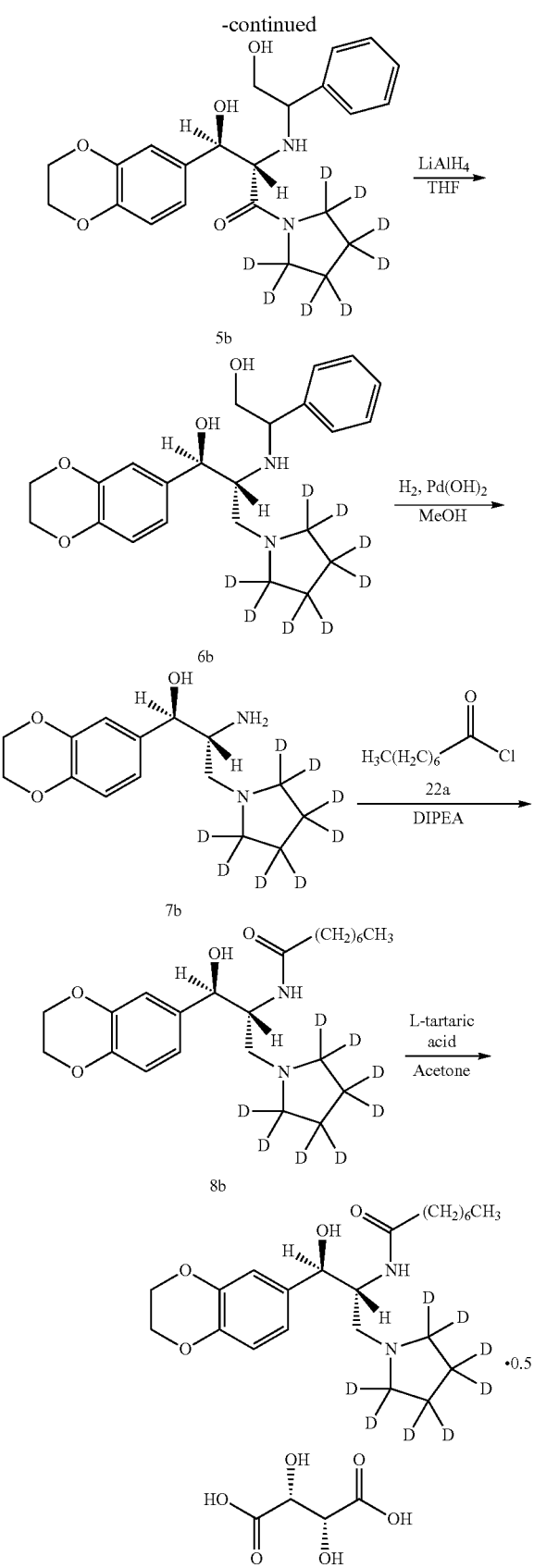

Compound 112. tartrate salt

Step 1. (2S,3R)-3-(2,3-Dihydrobenzo[b][1,4]dioxin-6-yl)-3-hydroxy-2-((2-hydroxy-1-phenylethyl)amino)-1-(pyrrolidin-1-yl-d8)propan-1-one (5b)

To a solution of compound 3a (6.16 g, 12.7 mmol) in dichloromethane (50 mL) was added pyrrolidine-2,2,3,3,4,4,5,5-$d_8$ (4b) (4.00 g, 50.6 mmol, Cambridge Isotope, 98 atom % D) and stirred at room temperature for 16 hours. The mixture was concentrated under reduced pressure, and the resulting residue was dissolved in methanol (50 mL) and concentrated under reduced pressure (process repeated 2×) affording a yellow oil which was dissolved in mixture of methanol (50 mL) and 1M HCl (50 mL) and refluxed for 4 hours, cooled, and stirred at room temperature for 16 hours. The mixture was concentrated under reduced pressure and the resulting aqueous mixture was washed with ethyl acetate (3×100 mL, discarded), adjusted to pH 8~9 with saturated sodium bicarbonate solution and extracted with ethyl acetate (3×100 mL). The combined organic layers were washed with saturated sodium chloride (100 mL), dried over sodium sulfate, filtered and concentrated under reduced pressure to afford 5b (3.6 g, 67% yield) as a beige foam, which was used directly for the next step without further purification.

Step 2. (1R,2R)-1-(2,3-Dihydrobenzo[b][1,4]dioxin-6-yl)-2-((2-hydroxy-1-phenylethyl)amino)-3-(pyrrolidin-1-yl-d8)propan-1-ol (6b)

To a solution of 5b (3.56 g, 8.48 mmol) in anhydrous THF (80 mL) at 0° C. was added a solution of 1.0M lithium aluminum hydride in THF (17 mL, 17 mmol). The reaction was stirred at room temperature for 2 days. The mixture was cooled to 0° C. and additional 1.0 M lithium aluminum hydride in THF (4 mL, 4 mmol, 0.5 equiv) was added. The mixture was stirred at room temperature for 16 hours, cooled to 0° C., quenched with 10% NaOH dropwise, diluted with water (100 mL), and extracted with ethyl acetate (3×100 mL). The combined organic layers were washed with saturated sodium chloride (100 mL), dried over sodium sulfate, filtered and concentrated under reduced pressure to afford 6b (3.59 g, quantitative yield) as an orange oil, which was used directly for the next step without further purification.

Step 3. (1R,2R)-2-Amino-1-(2,3-dihydrobenzo[b][1,4]dioxin-6-yl)-3-(pyrrolidin-1-yl-d8)propan-1-ol (7b)

To a solution of 6b (3.59 g, 8.5 mmol) in methanol (120 mL) was added trifluoroacetic acid (5 mL) and palladium hydroxide on carbon (0.36 g). The mixture was stirred under hydrogen (50 psi) for 16 hours at room temperature. Hydrogen was evacuated and replaced with nitrogen and the resulting mixture was filtered through a bed of celite, washed with methanol (40 mL) and the combined filtrate concentrated under reduced pressure. Water (100 mL) was added and the aqueous solution was washed with ethyl acetate (3×100 mL). The aqueous layer was adjusted to pH 12 with 50% NaOH and extracted with dichloromethane (3×50 mL). The combined organic layers were dried over sodium sulfate, filtered and concentrated under reduced pressure to afford 7b (0.61 g, 56% yield) as a light yellow wax, which was taken directly to the next step without further purification.

Step 4. N-((1R,2R)-1-(2,3-Dihydrobenzo[b][1,4]dioxin-6-yl)-1-hydroxy-3-(pyrrolidin-1-yl-d8)propan-2-yl)octanamide (8b)

To a solution of 7b (0.50 g, 1.75 mmol) in dichloromethane (10 mL) at 0° C. was added diisopropylethylamine (0.29 mL, 1.66 mmol), followed by dropwise addition of a solution of octanoyl chloride 22a (0.24 mL, 1.40 mmol) in dichloromethane (1 mL). The reaction was stirred at 0° C. for 2 hours, diluted with dichloromethane (5 mL) and 1N NaOH (5 mL) was added. The reaction mixture was stirred vigorously for 30 minutes at room temperature, extracted with dichloromethane (3×5 mL) and the combined organic layers were dried over sodium sulfate, filtered and concentrated under reduced pressure. The residue was purified by reverse phase chromatography on an AnaLogix automated chromatography system, eluting with a gradient of 0 to 50% acetonitrile in water. Product fractions were pooled and evaporated in vacuo to afford 8b (0.21 g, 29% yield) as a beige oil.

Step 5. N-(1R,2R)-1-(2,3-Dihydrobenzo[b][1,4]dioxin-6-yl)-1-hydroxy-3-(pyrrolidin-1-yl-d8)propan-2-yl)octanamide hemi-L-tartaric acid salt (Compound 112•tartrate)

To a solution of compound 8b (0.21 g, 0.51 mmol) in acetone (1.5 mL) at room temperature was added a solution of L-tartaric acid (0.038 g, 0.256 mmol) in acetone (1.5 mL) dropwise over 10 minutes. The mixture was stirred at room temperature for 30 minutes, 55° C. for 5 minutes and then room temperature for 30 minutes. The white precipitate that resulted was filtered, rinsed with small volumes of cold acetone and dried in vacuum oven at 30° C. for 16 hours to afford Compound 112•tartrate salt (188 mg, 65% yield) as a white solid. 1H NMR (DMSO-d6, 300 MHz) δ7.48-7.45 (d, J=9.1 Hz, 1H), 6.78-6.73 (m, 3H), 4.68-4.67 (m, 1H), 4.19 (s, 4H), 4.17-4.05 (m, 1H), 3.91 (s, 1H), 2.61-2.95 (m, 2H), 2.09-1.98 (m, 2H), 1.40-1.09 (m, 10H), 0.88 (m, 3H); MS (ESI) 413.4 [(M+H)+].

Example 3

N-(1R,2R)-1-(2,3-Dihydrobenzo[b][1,4]dioxin-6-yl)-1-hydroxy-3-(pyrrolidin-1-yl-d8)propan-2-yl)octanamide-d15 hemi-L-tartaric acid salt (Compound 114•tartrate salt)

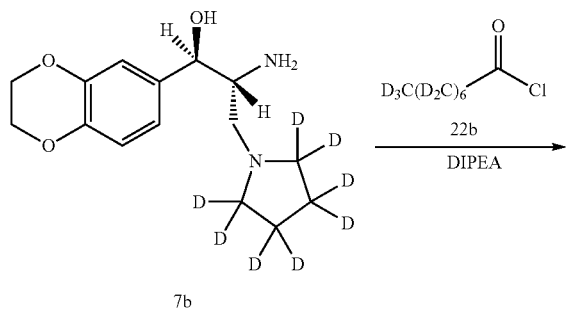

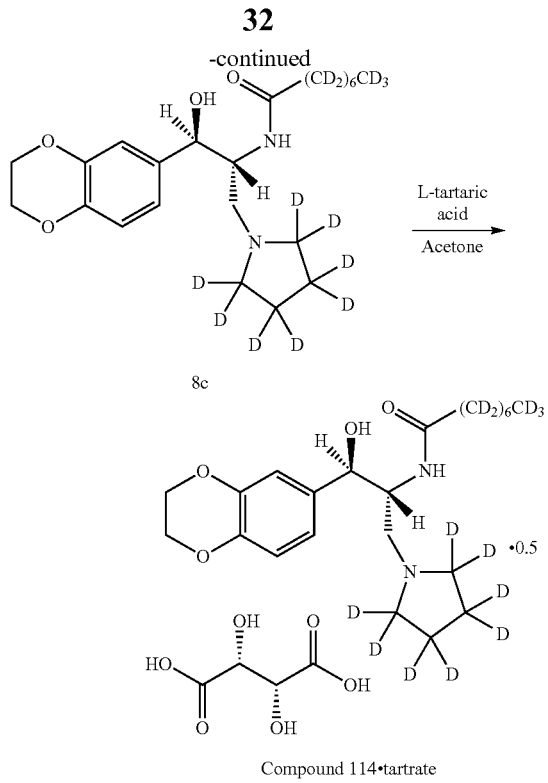

Step 1. N-((1R,2R)-1-(2,3-Dihydrobenzo[b][1,4]dioxin-6-yl)-1-hydroxy-3-(pyrrolidin-1-yl-d8)propan-2-yl)octanamide-d15 (8c)

To a solution of 7b (0.92 g, 3.22 mmol) and diisopropylethylamine (0.56 mL, 3.22 mmol, 1 equiv) in dichloromethane (10 mL) at 0° C. was added dropwise a solution of 22b (2.57 mmol) in dichloro-methane (1 mL). The mixture was stirred at 0° C. for 2 hours and concentrated under reduced pressure. The residue was purified by reverse phase chromatography on an AnaLogix automated chromatography system, eluting with a gradient of 0 to 50% acetonitrile in water. Product fractions were pooled and evaporated in vacuo to afford 8c (0.14 g, 10% yield) as a tan oil.

Step 2. N-(1R,2R)-1-(2,3-Dihydrobenzo[b][1,4]dioxin-6-yl)-1-hydroxy-3-(pyrrolidin-1-yl-d8)propan-2-yl)octanamide-d15 hemi-L-tartaric acid salt (114•tartrate salt)

To a solution of compound 8c (0.14 g, 0.32 mmol) in acetone (1 mL) at room temperature was added a solution of L-tartaric acid (0.024 g, 0.16 mmol) in acetone (1 mL) dropwise over 10 minutes. The mixture was stirred at room temperature for 30 minutes, 55° C. for 5 minutes and then room temperature for 30 minutes, at which time a white precipitate formed. The solid was filtered, rinsed with minimum cold acetone and dried in vacuum oven at 30° C. for 16 hours to give 114•tartrate salt (118 mg, 64% yield) as a white solid. 1H NMR (DMSO-d6, 300 MHz) δ7.49-7.46 (d, J=8.8 Hz, 1H), 6.78 (s, 1H), 6.72-6.72 (s, 2H), 4.67-4.66 (d, J=2.8 Hz, 1H), 4.18 (s, 4H), 4.08-4.16 (m, 1H), 3.92 (s, 1H), 2.98-2.92 (m, 1H0, 2.66-2.59 (m, 1H); MS (ESI) 428.4 [(M+H)+].

Example 4

N-(1R,2R)-1-(2,3-Dihydrobenzo[b][1,4]dioxin-6-yl-2,2,3,3-d4)-1-hydroxy-3-(pyrrolidin-1-yl)propan-2-yl)octanamide hemi-L-tartaric acid salt (Compound 103•tartrate salt)

Scheme 3a. Preparation of Compound 103•tartrate salt

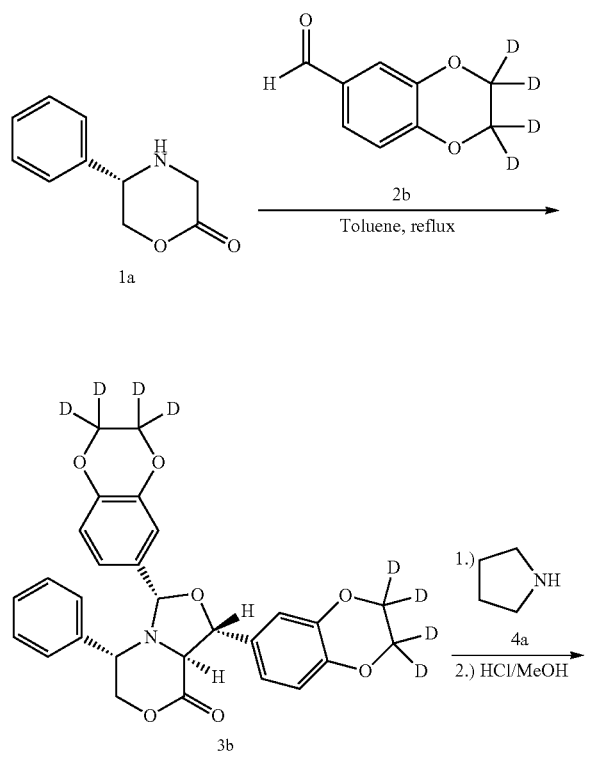

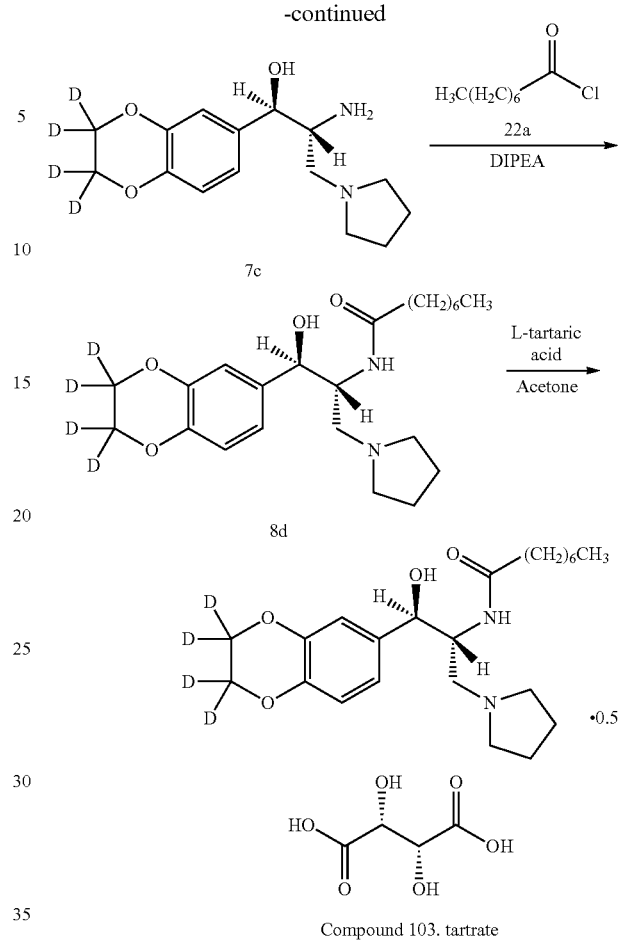

Preparation of 2,3-Dihydrobenzo[b][1,4]dioxine-2,2,3,3-d4-6-carbaldehyde (2b)

A mixture of 3,4-dihydroxybenzaldehyde (10a) (17.96 g, 130 mmol), 1,2-dibromoethane-d4 (50.0 g, 260 mmol, Cambridge Isotope, 99 atom % D) and cesium carbonate (84.8 g, 260 mmol) in dimethylformamide (160 mL) was heated at 70° C. for 16 hours. The mixture was cooled to room temperature, filtered. The resulting solid was washed with dichloromethane and the filtrate concentrated under reduced pressure. The crude product was purified on an AnaLogix automated chromatography system, eluting with a gradient of 10 to 25% ethyl acetate in heptanes. Product fractions were pooled and evaporated in vacuo to afford 2b (20.48 g, 94% yield) as a white solid.

Step 1. (1R,3S,5S,8aS)-1,3-Bis(2,3-dihydrobenzo[b][1,4]dioxin-6-yl-2,2,3,3-d4)-5-phenyltetrahydro-3H,8H-oxazolo[4,3-c][1,4]oxazin-8-one (3b)

To a solution of 1a (18.2 mL, 20.6 mmol) 1.13 M in benzene, 2b (10.4 g, 61.9 mmol) was added toluene (250 mL). The flask was equipped with Soxhlet extraction apparatus filled with activated 4 Å molecular sieves (20 g), refluxed vigorously for 2 days, cooled, and a solution of sodium metabisulfite (20 g) in water (80 mL) was added. The mixture was stirred vigorously for 1 hour and filtered. The layers of the filtrate were separated and the organic layer was washed with water (200 mL), saturated sodium chloride (200 mL), dried over sodium sulfate, filtered and concentrated under reduced pressure. The residue was purified on an AnaLogix automated chromatography system, eluting with a gradient of 0 to 50% ethyl acetate in heptanes. Product fractions were pooled and evaporated in vacuo and triturated with diethyl ether (60 mL) to afford 3b (3.48 g, 34% yield) as a white solid.

Step 2. (2S,3R)-3-(2,3-Dihydrobenzo b][1,4]dioxin-6-yl-2,2,3,3-d4)-3-hydroxy-2-((2-hydroxy-1-phenylethyl)amino)-1-(pyrrolidin-1-yl)propan-1-one (5c)

To a solution of compound 3b (2.00 g, 4.0 mmol) in dichloromethane (20 mL) was added pyrrolidine (4a) (1.7 mL, 20 mmol) and stirred at room temperature for 16 hours. The mixture was concentrated under reduced pressure and the residue dissolved in methanol (20 mL) and concentrated under reduced pressure (process repeated 2×). The residual yellow oil was dissolved in mixture of methanol (20 mL), 1M aqueous HCl (20 mL) and refluxed for 4 hours, cooled and stirred at room temperature for 16 hours. The mixture was concentrated under reduced pressure and diluted with ethyl acetate (50 mL) and stirred at room temperature for 30 minutes. The layers were separated and the organic layer was washed with 1N HCl (50 mL). The combined aqueous layer was washed with ethyl acetate (2×50 mL), adjusted to pH 8~9 with saturated sodium bicarbonate solution and extracted with ethyl acetate (3×50 mL). The combined organic layers were washed with saturated sodium chloride (50 mL), dried over sodium sulfate, filtered and concentrated under reduced pressure to afford 5c (1.5 g, 90% yield) as a white solid, which was taken directly to the next step without further purification.

Step 3. (1R,2R)-1-(2,3-Dihydrobenzo[b][1,4]dioxin-6-yl-2,2,3,3-d4)-2-((2-hydroxy-1-phenylethyl)amino)-3-(pyrrolidin-1-yl)propan-1-ol (6c)

To a solution of compound 5c (1.50 g, 3.6 mmol) in anhydrous THF (30 mL) at 0° C. was added a solution of 1.0M lithium aluminum hydride in THF (7.2 mL, 7.2 mmol). The mixture was stirred at room temperature for 16 hours. The reaction was cooled to 0° C. and additional 1.0M lithium aluminum hydride in THF (1.8 mL, 1.8 mmol) was added. The mixture was stirred at room temperature for a further 16 hours, cooled to 0° C., quenched with dropwise addition of 10% NaOH, diluted with water (50 mL) and extracted with ethyl acetate (3×50 mL). The combined organic layer was washed with saturated sodium chloride (50 mL), dried over sodium sulfate, filtered and concentrated under reduced pressure to give 6c (1.5 g, quantitative yield) as a beige colored wax, which was taken directly to the next step without further purification.

Step 4. (1R,2R)-2-Amino-1-(2,3-dihydrobenzo[b][1,4]dioxin-6-yl-2,2,3,3-d4)-3-(pyrrolidin-1-yl)propan-1-ol (7c)

To a solution of 6c (1.5 g, 3.8 mmol) in methanol (50 mL) was added trifluoroacetic acid (2 mL), followed by palladium hydroxide on carbon (0.15 g). The reaction was stirred under hydrogen gas (50 psi) at room temperature for 16 hours. Hydrogen was evacuated and replaced with nitrogen and the resulting mixture was filtered through a bed of celite and concentrated under reduced pressure. Water (50 mL) was added and the aqueous solution was washed with ethyl acetate (3×50 mL). The aqueous layer was adjusted to pH 12 with 50% NaOH, extracted with dichloromethane (3×50 mL) and the combined organic layer was dried over sodium sulfate, filtered and concentrated under reduced pressure to furnish 7c (0.61 g, 56% yield) as a light yellow wax, which was taken directly to the next step without further purification.

Step 5. N-((1R,2R)-1-(2,3-Dihydrobenzo[b][1,4]dioxin-6-yl-2,2,3,3-d4)-1-hydroxy-3-(pyrrolidin-1-yl)propan-2-yl)octanamide (8d)

To a solution of 7c (0.32 g, 1.13 mmol) in dichloromethane (4 mL) at 0° C. was added diisopropylethylamine (0.20 mL, 1.13 mmol). Octanoyl chloride 22a (0.15 mL, 0.91 mmol) in dichloromethane (1 mL) was added dropwise and the mixture was stirred at 0° C. for 2 hours. Dichloromethane (5 mL) and 1N NaOH (5 mL) were added and the mixture was stirred vigorously for 30 minutes at room temperature, extracted with dichloromethane (3×5 mL) and the combined organic layer was dried over sodium sulfate, filtered and concentrated under reduced pressure. The residue was purified by reverse phase chromatography on an AnaLogix automated chromatography system, eluting with a gradient of 0 to 50% acetonitrile in water. Product fractions were pooled and evaporated in vacuo to afford 8d (111 mg, 24% yield) as a clear wax.

Step 6. N-((1R,2R)-1-(2,3-Dihydrobenzo[b][1,4]dioxin-6-yl-2,2,3,3-d4)-1-hydroxy-3-(pyrrolidin-1-yl)propan-2-yl)octanamide hemi-L-tartaric acid salt (Compound 103•tartrate salt)

To a solution of compound 8d (0.111 g, 0.272 mmol, 1 equiv) in acetone (1 mL) at room temperature was added a solution of L-tartaric acid (0.020 g, 0.135 mmol, 0.497 equiv) in acetone (1 mL) dropwise over 10 minutes. The reaction was stirred at room temperature for 30 minutes, 55° C. for 5 minutes then room temperature for 30 minutes, at which time a white precipitate formed. The solid was filtered, rinsed with minimum cold acetone and dried in vacuum oven at 30° C. for 16 hours to afford Compound 103•tartrate salt (106 mg, 70% yield) as a white solid. 1H NMR (DMSO-d6, 300 MHz) δ7.46-7.43 (d, J=8.8 Hz, 1H), 6.78-6.73 (m, 3H), 4.68-4.66 (d, J=2.64 Hz, 1H), 4.09-4.06 (m, 1H), 3.93 (s, 1H), 2.92-2.86 (m, 1H), 2.73 (br, m, 4H), 2.04-1.96 (m, 2H), 1.75 (br, m, 4H), 1.37-1.09 (m, 10H), 0.88-0.83 (m, 3H); MS (ESI) 409.2 [(M+H)+].

Example 5

N-((1R,2R)-1-(2,3-dihydrobenzo[b][1,4]dioxin-6-yl-2,2,3,3-d4)-1-hydroxy-3-(pyrrolidin-1-yl)propan-2-yl)octan-d15-amide hemi-L-tartaric acid salt (Compound 105•tartrate salt)

Scheme 3b. Preparation of Compound 105•tartrate salt

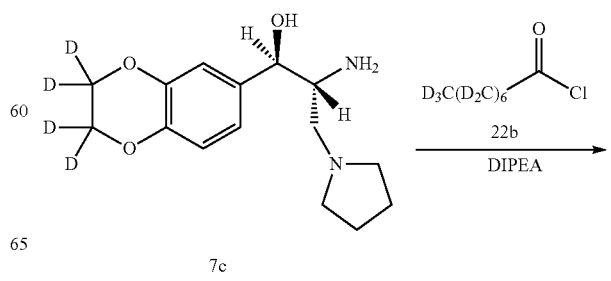

7c

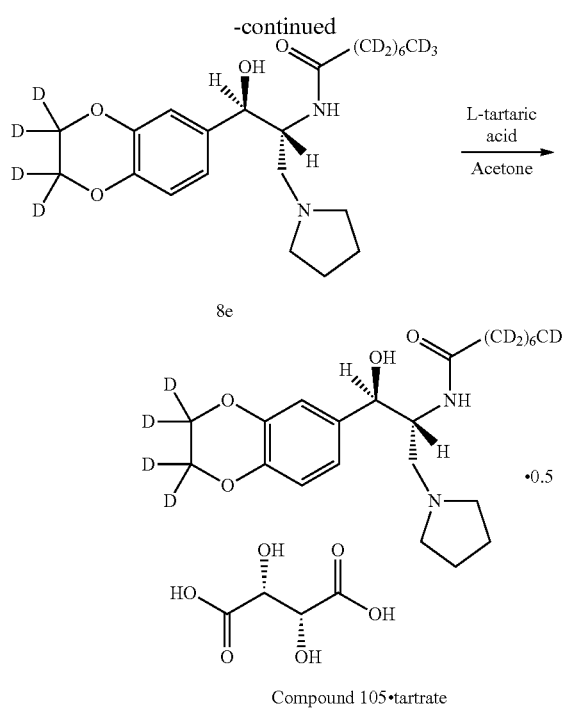

Compound 105•tartrate

Step 1. N-((1R,2R)-1-(2,3-dihydrobenzo[b][1,4]dioxin-6-yl-2,2,3,3-d4)-1-hydroxy-3-(pyrrolidin-1-yl)propan-2-yl)octan-d15-amide (8e)

To a solution of 7c (0.70 g, 2.48 mmol) in dichloromethane (15 mL) was added diisopropylethylamine (0.41 mL, 2.35 mmol), followed by a dropwise addition of a solution of 22b (0.35 g, 1.98 mmol) in dichloromethane (5 mL), and the mixture was stirred at 0° C. for 2 hours and at room temperature for 2 hours. 10% NaOH (20 mL) was added and the biphasic mixture was stirred for 1 hour. The layers were separated and the aqueous layer was extracted with dichloromethane (2×35 mL). The combined organic layer was dried over sodium sulfate, filtered and concentrated under reduced pressure. The residue was purified by reverse phase chromatography on an AnaLogix automated chromatography system, eluting with a gradient of 0 to 50% acetonitrile in water. Product fractions were pooled and evaporated in vacuo to afford 8e (0.325 g, 39% yield) as a yellow oil.

Step 2. N-(1R,2R)-1-(2,3-dihydrobenzo[b][1,4]dioxin-6-yl-2,2,3,3-d4)-1-hydroxy-3-(pyrrolidin-1-yl)propan-2-yl)octan-d15-amide hemi-L-tartaric acid salt (Compound 105•tartrate salt)

L-tartaric acid (57.6 mg, 0.38 mmol) was dissolved in acetone (1 mL) at 55° C. and was added to a solution of 8e (325 mg, 0.77 mmol) in acetone (3 mL) at room temperature. The mixture was stirred at room temperature for 30 minutes, at 55° C. for 10 minutes and room temperature for 30 minutes. The solid that formed was filtered, washed with cold acetone (4 mL) and dried in a vacuo at room temperature for 2 days to afford Compound 105•tartrate salt (285 mg, 75% yield) as a white solid. 1H NMR (DMSO-$d_6$, 300 MHz) δ7.49-7.46 (d, J=9.1 Hz, 1H), 6.78-6.73 (m, 3H), 4.68-4.67 (d, J=2.6 Hz, 1H), 4.09-4.07 (m, 1H), 3.94 (s, 1H), 2.93-2.92 (m, 1H), 2.90-2.74 (m, 4H), 2.59-2.55 (m, 1H), 1.63-1.75 (m, 4H); MS (ESI) 424.3 [(M+H)+].

Example 6

N-((1R,2R)-1-(2,3-Dihydrobenzo[b][1,4]dioxin-6-yl-2,2,3,3-d4)-1-hydroxy-3-(pyrrolidin-1-yl-d8)propan-2-yl)octanamide hemi-L-tartaric acid salt (Compound 118•tartrate salt)

Scheme 4a. Preparation of Compound 118•tartate salt

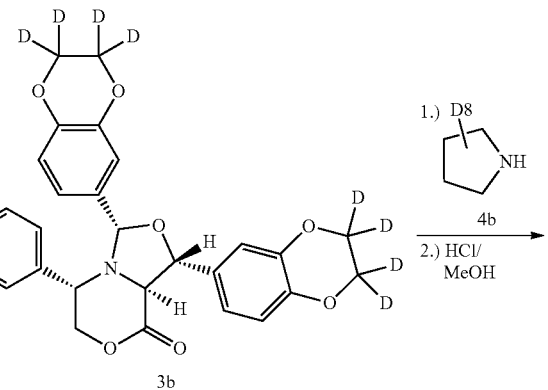

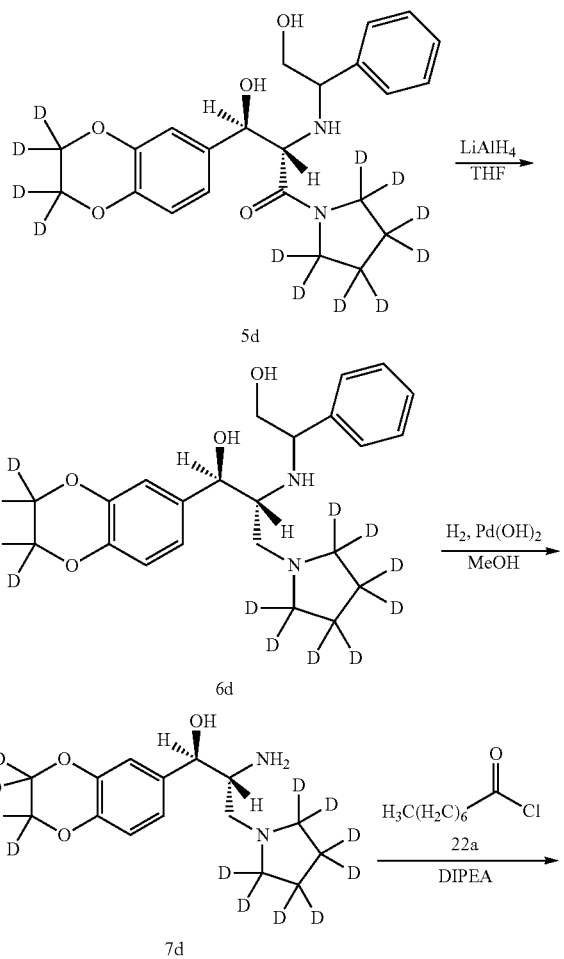

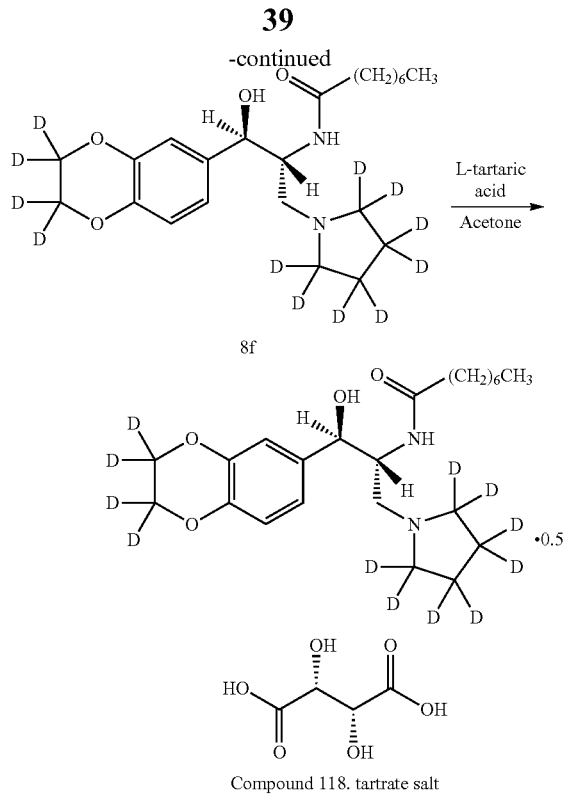

Compound 118. tartrate salt

Step 1. (2S,3R)-3-(2,3-Dihydrobenzo[b][1,4]dioxin-6-yl-2,2,3,3-d4)-3-hydroxy-2-((2-hydroxy-1-phenyl-ethyl)amino)-1-(pyrrolidin-1-yl-d8)propan-1-one (5d)

To a solution of 3b (3.13 g, 6.33 mmol) in dichloromethane (25 mL) was added pyrrolidine 2,2,3,3,4,4,5,5,-d8 (4b) (2.00 g, 25.32 mmol, CDN Isotopes, 98 atom % D) and was stirred at room temperature for 16 hours. The mixture was concentrated under reduced pressure and the residue was dissolved in methanol (25 mL) and concentrated under reduced pressure (process repeated 2×). The residual yellow oil was dissolved in mixture of methanol (25 mL), 1M HCl (25 mL) and the mixture was refluxed for 4 hours, cooled to room temperature, and stirred for 16 hours. The mixture was concentrated under reduced pressure and the residual aqueous solution was washed with ethyl acetate (3×500 mL), adjusted to pH 8~9 with saturated sodium bicarbonate solution and extracted with ethyl acetate (3×50 mL). The combined organic layer was washed with saturated sodium chloride (50 mL), dried over sodium sulfate, filtered and concentrated under reduced pressure to afford 5d (1.8 g, 69% yield) as a beige foam, which was taken directly to the next step without further purification.

Step 2. (1R,2R)-1-(2,3-Dihydrobenzo[b][1,4]dioxin-6-yl-2,2,3,3-d4)-2-((2-hydroxy-1-phenylethyl)amino)-3-(pyrrolidin-1-yl-d8)propan-1-ol (6d)

To a solution of 5d (2.76 g, 6.51 mmol) in anhydrous THF (60 mL) at 0° C. was added a solution of 1.0M lithium aluminum hydride in THF (13 mL, 13 mmol). The mixture was stirred at room temperature for 16 hours. The reaction was cooled to 0° C. and additional 1.0M lithium aluminum hydride in THF (3.3 mL, 3.2 mmol) was added and the mixture was stirred at room temperature for a further 16 hours, cooled to 0° C., and quenched with 10% NaOH. The mixture was diluted with water (100 mL), extracted with ethyl acetate (3×100 mL) and the combined organic layer was washed with saturated sodium chloride (100 mL), dried over sodium sulfate, filtered and concentrated under reduced pressure to give 6d (2.84 g, quantitative yield) as an orange oil, which was taken directly to the next step without further purification.

Step 3. (1R,2R)-2-Amino-1-(2,3-dihydrobenzo[b][1,4]dioxin-6-yl-2,2,3,3-d4)-3-(pyrrolidin-1-yl-d8)propan-1-ol (7d)

To a solution of 6d (2.84 g, 6.93 mmol) in methanol (100 mL) and trifluoroacetic acid (4 mL) was added palladium hydroxide on carbon (0.28 g). The mixture was stirred under hydrogen (50 psi) at room temperature for 16 hours. The mixture was filtered through a bed of celite, concentrated under reduced pressure and water (100 mL) was added. The aqueous solution was washed with ethyl acetate (3×100 mL) and the aqueous layer was adjusted to pH 12 with 50% NaOH and extracted with dichloromethane (3×50 mL). The combined organic layer was dried over sodium sulfate, filtered and concentrated under reduced pressure to give 7d (1.2 g, 60% yield) as an amber oil, which was taken directly to the next step without further purification.

Step 4. N-(1R,2R)-1-(2,3-Dihydrobenzo[b][1,4]dioxin-6-yl-2,2,3,3-d4)-1-hydroxy-3-(pyrrolidin-1-yl-d8)propan-2-yl)octanamide (8f)

To a solution of 7d (0.60 g, 2.16 mmol) in dichloromethane (10 mL) at 0° C. was added diisopropylethylamine (0.36 mL, 2.05 mmol), followed by a dropwise addition of a solution of octanoyl chloride (0.30 mL, 1.73 mmol) in dichloromethane (1 mL). The mixture was stirred at 0° C. for 2 hours, concentrated under reduced pressure and the residue was purified by reverse phase chromatography on an AnaLogix automated chromatography system, eluting with a gradient of 0 to 50% acetonitrile in water. Product fractions were pooled and evaporated in vacuo to afford 8f (0.13 g, 14% yield) as a beige colored oil.

Step 5. N-(1R,2R)-1-(2,3-Dihydrobenzo[b][1,4]dioxin-6-yl-2,2,3,3-d4)-1-hydroxy-3-(pyrrolidin-1-yl-d8)propan-2-yl)octanamide hemi-L-tartaric acid salt (Compound 118•tartrate salt)

To a solution of 8f (0.132 g, 0.313 mmol) in acetone (1 mL) at room temperature was added a solution of L-tartaric acid (0.023 g, 0.155 mmol) in acetone (1 mL) dropwise over 10 minutes. The mixture was stirred at room temperature for 30 minutes, 55° C. for 5 minutes and room temperature for 30 minutes, at which time a white precipitate formed. The solid was filtered, rinsed with small amounts of cold acetone and dried in vacuum oven at 30° C. for 16 hours to afford Compound 118•tartrate salt (108 mg, 61% yield) as a white solid. 1H NMR (DMSO-d6, 300 MHz) δ 7.49-7.47 (d, J=7.8 Hz, 1H), 6.78-6.72 (m, 3H), 4.66 (m, 1H), 4.27-4.08 (m, 1H), 3.92 (s, 1H), 2.61-2.95 (m, 2H), 1.96-2.06 (m, 2H), 1.07-1.33 (m, 12H), 0.82-0.87 (m, 3); MS (ESI) 417.3 [(M+H)+].

Example 7

N-((1R,2R)-1-(2,3-Dihydrobenzo[b][1,4]dioxin-6-yl-2,2,3,3-d4)-1-hydroxy-3-(pyrrolidin-1-yl-d8)propan-2-yl)octanamide-d15 hemi-L-tartaric acid salt (Compound 120•tartrate salt)

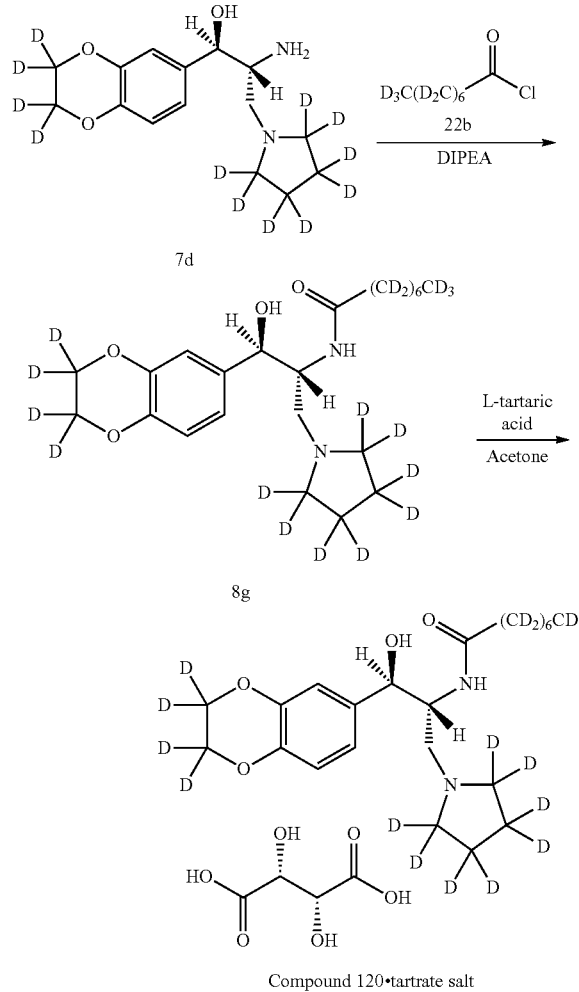

Step 1. N-(1R,2R)-1-(2,3-Dihydrobenzo[b][1,4]dioxin-6-yl-2,2,3,3-d4)-1-hydroxy-3-(pyrrolidin-1-yl-d8)propan-2-yl)octanamide-d15 (8g)

To a solution of 7d (0.59 g, 2.03 mmol) and diisopropylethylamine (0.35 mL, 2.03 mmol) in dichloromethane (10 mL) at 0° C. was added dropwise a solution of 22b (1.63 mmol) in dichloromethane (1 mL). The mixture was stirred at 0° C. for 2 hours and concentrated under reduced pressure. The residue was purified by reverse phase chromatography on an AnaLogix automated chromatography system, eluting with a gradient of 0 to 50% acetonitrile in water. Product fractions were pooled and evaporated in vacuo to afford 8g (90 mg, 10% yield) as a tan wax.

Step 2. N-((1R,2R)-1-(2,3-Dihydrobenzo[b][1,4]dioxin-6-yl-2,2,3,3-d4)-1-hydroxy-3-(pyrrolidin-1-yl-d8)propan-2-yl)octanamide-d15 hemi-L-tartaric acid (Compound 120•tartrate salt)

To a solution of compound 8g (0.090 g, 0.209 mmol) in acetone (1 mL) at room temperature was added a solution of L-tartaric acid (0.016 g, 0.104 mmol) in acetone (1 mL) dropwise over 10 minutes. The reaction was stirred at room temperature for 30 minutes, 55° C. for 5 minutes and room temperature for 30 minutes, at which time a white precipitate formed. The solid was filtered, rinsed with minimum cold acetone, triturated with dichloromethane/MTBE and dried in vacuum oven at 30° C. for 16 hours to afford Compound 120•tartrate salt (46 mg, 38% yield) as a beige solid. 1H NMR (DMSO-$d_6$, 300 MHz) δ 7.51-7.48 (d, J=9.1 Hz, 1H), 6.79 (s, 1H), 6.74-6.73 (s, 2H), 4.67-4.66 (d, J=2.6 Hz, 1H), 4.10-4.21 (m, 1H), 3.96 (s, 1H), 3.08-3.00 (m, 1H), 2.98-2.57 (m, 1H); MS (ESI) 432.3 [(M+H)+].

Example 8

N-(1R,2R)-1-(2,3-Dihydrobenzo[b][1,4]dioxin-6-yl)-1-hydroxy-3-(pyrrolidin-1-yl)propan-2-yl-1-d)octanamide hemi-L-tartaric acid salt (Compound 142•tartate salt)

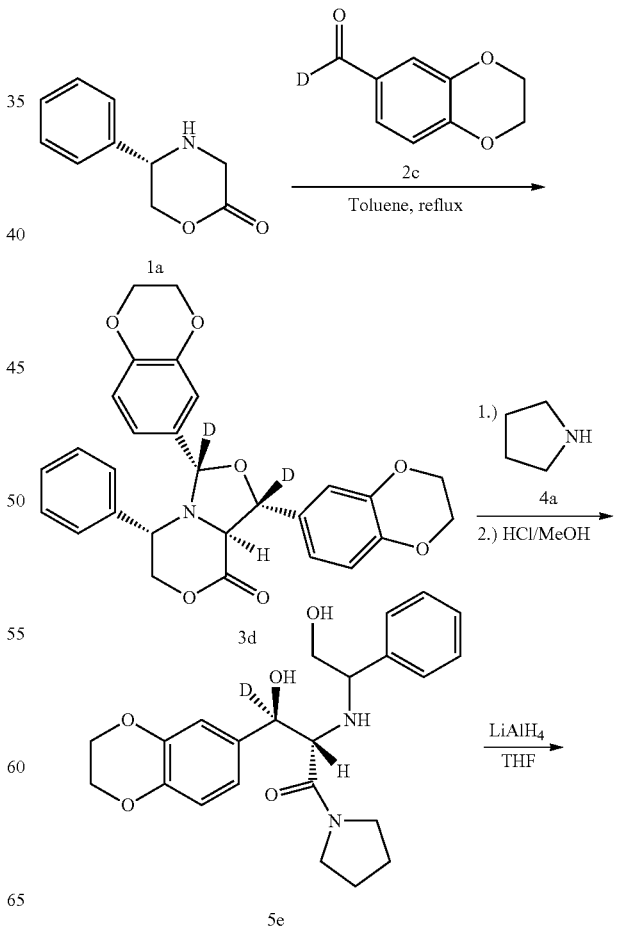

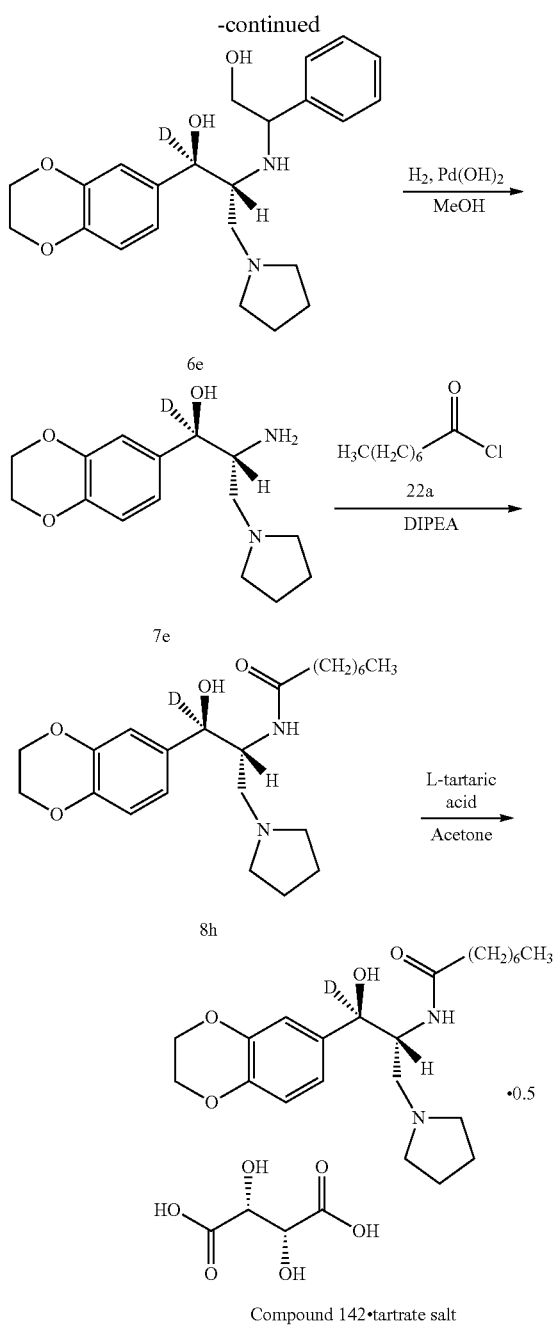

Compound 142•tartrate salt

Preparation of Intermediate
2,3-Dihydrobenzo[b][1,4]dioxine-6-carbaldehyde-d
(2c)

a) Preparation of N-Methoxy-N-methyl-2,3-dihydrobenzo[b][1,4]dioxine-6-carboxamide)

To a suspension of 1,4-benzodioxane-6-carboxylic acid (17.0 g, 94.3 mmol) in acetonitrile (150 mL) was added 1,1'-carbonyldiimidazole (16.1 g, 99.1 mmol). The mixture was stirred at room temperature for 20 minutes. In a second flask, a solution of N,O-dimethyl hydroxylamine hydrochloride (18.4 g, 188.7 mmol) and triethylamine (26.3 mL, 188.7 mmol) in acetonitrile (40 mL) was stirred at room temperature for 30 minutes then added to the contents of the first flask. The reaction mixture was heated at 40° C. for 18 hours, filtered and concentrated under reduced pressure. The residue was partitioned between water (50 mL) and dichloromethane (200 mL). The organic layer was washed with water (40 mL), 5% HCl (40 mL), saturated sodium bicarbonate solution (40 mL) and saturated sodium chloride (40 mL). The mixture was dried over sodium sulfate, filtered concentrated under reduced pressure and dried in vacuum oven at 30° C. for 2 hours to afford N-methoxy-N-methyl-2,3-dihydrobenzo[b][1,4]dioxine-6-carboxamide (19.52 g, 93% yield) as a white solid, which was taken directly to the next step without further purification.

b1) Preparation of
2,3-Dihydrobenzo[b][1,4]dioxine-6-carbaldehyde-d
(2c) Via LiAlD$_4$ Reduction To a solution of compound N-methoxy-N-methyl-2,3-dihydrobenzo[b][1,4]dioxine-6-carboxamide (27.4 g, 122.9 mmol) in anhydrous THF (540 mL) at −30° C. was added solid lithium aluminum deuteride (5.2 g, 122.9 mmol, ARMAR Chemicals, 98 atom % D) in portions. The mixture was stirred at −30° C. for 2 hours, quenched with 5% HCl at 0° C. and extracted with ethyl acetate (3×400 mL). The combined organic layer was washed with saturated sodium chloride (500 mL), dried over sodium sulfate, filtered and concentrated under reduced pressure. The residue was purified on an AnaLogix automated chromatography system, eluting with a gradient of 0 to 30% ethyl acetate in heptanes. Product fractions were pooled and evaporated in vacuo to afford 2c (14.1 g, 69% yield) as a white solid.

b2) Alternate Preparation of
2,3-Dihydrobenzo[b][1,4]dioxine-6-carbaldehyde-d
(2c) Via DIBAL-D Reduction To a solution of N-methoxy-N-methyl-2,3-dihydrobenzo[b][1,4]dioxine-6-carboxamide (15.0 g, 67.3 mmol) in tetrahydrofuran (300 mL) at −70° C. was added a 0.7M diisobutylaluminun deuteride in toluene (100 mL, 70 mmol, Aldrich, 98 atom % D) over 25 minutes. The mixture was stirred at −30 to −20° C. for 4 hours, 1M HCl (230 mL) was added and the mixture was diluted with water (200 mL), extracted with ethyl acetate (3×250 mL). The combined organic layer was washed with saturated sodium chloride (150 mL), dried over sodium sulfate and concentrated under reduced pressure. The residue was purified on an AnaLogix automated chromatography system eluting with a gradient of 0 to 16% ethyl acetate in heptanes. Product fractions were pooled and evaporated in vacuo to afford 2c (9.18 g, 83% yield) as a white solid.

Step 1. (1R,3S,5S,8aS)-1,3-Bis(2,3-dihydrobenzo[b][1,4]dioxin-6-yl)-5-phenyltetrahydro-3H,8H-oxazolo[4,3-c][1,4]oxazin-8-one-1,3-d2 (3d)

To a solution of 2,3-Dihydrobenzo[b][1,4]dioxine-6-carbaldehyde-d (2d) (9.18 g, 55.6 mmol) in anhydrous toluene (250 mL) was added a 1.13M solution of 1a in benzene (16.4 mL, 18.5 mmol). The reaction mixture, equipped with a Soxhlet extractor filled with activated 4 Å molecular sieves (60 g), was refluxed vigorously for 3 days, and cooled to room temperature. A solution of sodium metabisulfite (17.6 g) in water (42 mL) was added and the mixture was stirred for 1 hour. A white solid was filtered, washed with ethyl acetate and the filtrate was placed in a separatory funnel and the layers separated. The organic layer was washed with water (100 mL) and saturated sodium chloride (80 mL), dried over sodium sulfate, filtered, concentrated under reduced pressure and dried in a vacuo at room temperature to furnish a brown solid (8.5 g). The solid was triturated with diethyl ether (120 mL) overnight, filtered and washed with diethyl ether (60 mL) to give a yellow solid (3.8 g) which was further purified on an AnaLogix automated chromatography system (120 g), eluting with a gradient of 10 to 45% ethyl acetate in heptanes. Product fractions were pooled and evaporated in vacuo to afford 3d (2.77 g, 31% yield) as a yellow foam.

Step 2. (2S,3R)-3-(2,3-Dihydrobenzo[b][1,4]dioxin-6-yl)-3-hydroxy-2-((2-hydroxy-1-phenylethyl)amino)-1-(pyrrolidin-1-yl)propan-1-one-3-d (5e)

Pyrrolidine 4a (4.3 mL, 51.5 mmol) was added to a solution of 3d (5.02 g, 10.3 mmol) in dichloromethane (60 mL). The mixture was stirred at room temperature overnight and concentrated under reduced pressure. The residue was dissolved in methanol (20 mL) and concentrated under reduced pressure (process repeated 2x). The residual yellow oil was dissolved in mixture of methanol (55 mL) and 1M HCl (55 mL) and refluxed for 4 hours, cooled to room temperature and concentrated under reduced pressure. Ethyl acetate (70 mL) was added and the mixture was stirred for 30 minutes. The layers were separated and the organic layer was extracted with 1M HCl (80 mL). The combined aqueous layers were washed twice with ethyl acetate (2×45 mL), adjusted with 1M NaOH to pH 5 and saturated sodium bicarbonate solution to pH 8. The aqueous mixture was extracted three times with ethyl acetate (3×120 mL). The combined organic layers were washed with saturated sodium chloride (50 mL), dried over sodium sulfate, filtered and concentrated under reduced pressure to give 5e (3.23 g, 76% yield) as a white foam which was taken directly to the next step without further purification.

Step 3. (1R,2R)-1-(2,3-Dihydrobenzo[b][1,4]dioxin-6-yl)-2-((2-hydroxy-1-phenylethyl)amino)-3-(pyrrolidin-1-yl)propan-1-d-1-ol (3d)

To a solution of 5e (0.80 g, 1.9 mmol) in anhydrous THF (18 mL) at 0° C. was added a 1.0M solution of lithium aluminum hydride in THF (4.8 mL, 4.8 mmol). The mixture was stirred at room temperature for 20 hours. The mixture was cooled to 0° C. and additional 1.0M lithium aluminum hydride solution in THF (2.4 mL, 2.4 mmol) was added. The mixture was stirred at room temperature for a further 20 hours, cooled to 0° C. and quenched with 10% NaOH. The mixture was diluted with water (30 mL), extraction with ethyl acetate (60 mL, 30 mL, 20 mL) and the combined organic layer was washed with saturated sodium chloride (15 mL), dried over sodium sulfate, filtered and concentrated under reduced pressure to give 3d (0.70 g, 91% yield) as a yellow oil, which was taken directly to the next step without further purification.

Step 4. (1R,2R)-2-Amino-1-(2,3-dihydrobenzo[b][1,4]dioxin-6-yl)-3-(pyrrolidin-1-yl)propan-1-d-1-ol (7e)

To a solution of 3d (0.70 g, 1.75 mmol) in methanol (40 mL) was added palladium hydroxide on carbon (140 mg), trifluoroacetic acid (4 mL), and water (3 mL). The mixture was stirred under hydrogen (50 psi) at room temperature for 16 hours. The mixture was filtered through a bed of celite and the filtrate was concentrated under reduced pressure. Water (40 mL) was added and the aqueous solution was washed with ethyl acetate (3×25 mL). The aqueous layer was adjusted to pH 12 with a 24% NaOH, extracted with dichloromethane (3×25 mL) and the combined organic layer was dried over sodium sulfate, filtered and concentrated under reduced pressure. The residue was dissolved in chloroform (20 mL) and concentrated under reduced pressure and dried in a vacuo at room temperature to afford 7e (0.35 g, 71% yield) as a colorless oil, which was taken directly to the next step without further purification.

Step 5. N-(1R,2R)-1-(2,3-Dihydrobenzo[b][1,4]dioxin-6-yl)-1-hydroxy-3-(pyrrolidin-1-yl)propan-2-yl-1-d)octanamide (8h)

A solution of octanoyl chloride 22a (0.16 g, 1.00 mmol) in dichloromethane (3 mL) was added dropwise to a cooled solution of 7e (0.35 g, 1.25 mmol) and diisopropylethylamine (0.21 mL, 1.19 mmol) in dichloromethane (10 mL), and the mixture stirred at 0° C. for 1 hour and at room temperature for 2 hours. 10% NaOH (10 mL) was added and the biphasic mixture was stirred for 1 hour. The layers were separated and the aqueous layer was extracted with dichloromethane (3×25 mL). The combined organic layer was dried over sodium sulfate, filtered and concentrated under reduced pressure. The residue was purified by reverse phase chromatography on an AnaLogix automated chromatography system, eluting with a gradient of 0 to 50% acetonitrile in water. Product fractions were pooled and evaporated in vacuo to afford 8h (0.068 g, 17% yield) as a colorless oil.

Step 6. N-(1R,2R)-1-(2,3-Dihydrobenzo[b][1,4]dioxin-6-yl)-1-hydroxy-3-(pyrrolidin-1-yl)propan-2-yl-1-d)octanamide hemi-L-tartaric acid salt (Compound 142•tartate salt)

L-tartaric acid (12.6 mg, 0.084 mmol) was dissolved in acetone (0.5 mL) at 55° C. This solution was added to a solution of 8h (68 mg, 0.17 mmol) in acetone (1.5 mL) at room temperature and the mixture was stirred at room temperature for 30 minutes, 55° C. for 10 minutes, and room temperature overnight. The mixture was left standing in a freezer for 3 days and a white precipitate was obtained. The solid was filtered, washed with cold acetone (3 mL) and dried in a vacuo at room temperature for 30 hours to give Compound 142•tartate salt (57 mg, 71% yield) as a white solid. 1H NMR (DMSO-$d_6$, 300 MHz) δ7.48-7.45 (d, J=9.1 Hz, 1H), 6.77 (s, 1H), 6.76-6.71 (m, 2H), 4.17-4.10 (s, 4H), 4.02-4.07 (m, 1H), 3.92 (s, 1H), 2.93-2.89 (m, 1H), 2.73-2.87 (m, 4H), 2.55-2.58 (m, 1H), 2.07-2.04 (m, 2H), 1.73-1.91 (m, 4H), 1.36-1.04 (m, 10H), 0.86-0.81 (m, 3); MS (ESI) 406.1 [(M+H)+].

Example 9

N-((1R,2R)-1-(2,3-Dihydrobenzo[b][1,4]dioxin-6-yl)-1-hydroxy-3-(pyrrolidin-1-yl)propan-2-yl-1-d)octan-d15-amide hemi-L-tartaric acid salt (Compound 144•tartate salt)

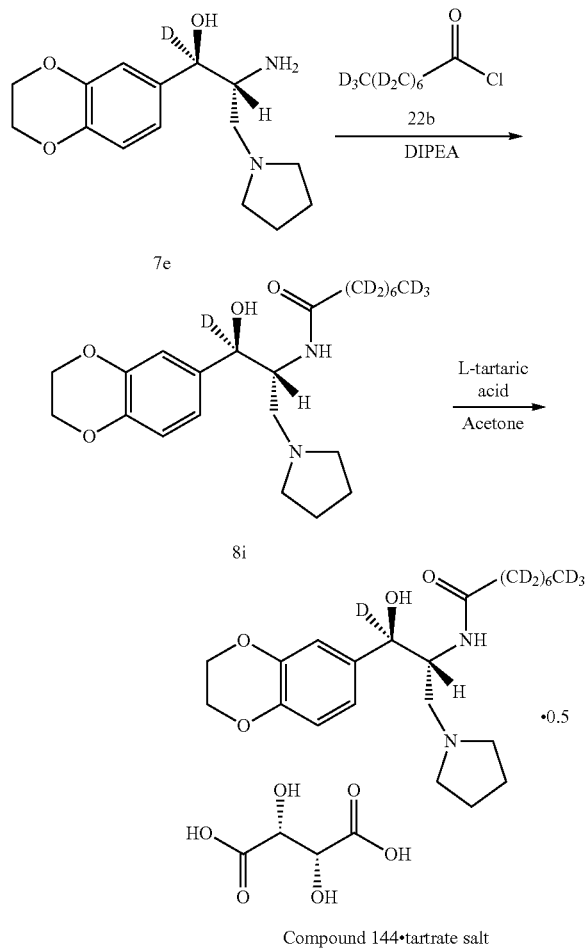

Step 1. N-((1R,2R)-1-(2,3-Dihydrobenzo[b][1,4]dioxin-6-yl)-1-hydroxy-3-(pyrrolidin-1-yl)propan-2-yl-1-d)octan-d15-amide (8i)

A solution of 22b (0.23 g, 1.29 mmol) in dichloromethane (5 mL) was added dropwise to a solution of 7e (0.45 g, 1.61 mmol) and diisopropylethylamine (0.27 mL, 1.53 mmol) in dichloromethane (10 mL) at 0° C. and the mixture stirred at 0° C. for 3 hours. 10% NaOH (15 mL) was added and the biphasic mixture was stirred for 1 hour. The layers were separated and the aqueous layer was extracted with dichloromethane (3×25 mL) and the combined organic layer was dried over sodium sulfate, filtered, and concentrated under reduced pressure. The residue was purified by reverse phase chromatography on an AnaLogix automated chromatography system, eluting with a gradient of 0 to 50% acetonitrile in water. Product fractions were pooled and evaporated in vacuo to give 8i (0.26 g, 38% yield) as a colorless oil.

Step 2. N-(1R,2R)-1-(2,3-Dihydrobenzo[b][1,4]dioxin-6-yl)-1-hydroxy-3-(pyrrolidin-1-yl)propan-2-yl-1-d)octan-d15-amide hemi-L-tartaric acid salt (Compound 144•tartate salt)

L-tartaric acid (45.5 mg, 0.30 mmol) was dissolved in acetone (1 mL) at 55° C. This solution was added to a solution of 8i (261 mg, 0.62 mmol) in acetone (3 mL) at room temperature and the mixture was stirred at room temperature for 30 minutes, 55° C. for 10 minutes, room temperature for 30 minutes and 0° C. for 20 minutes resulting in a white precipitate. The solids were filtered, washed with cold acetone (3 mL) and dried in a vacuo at room temperature for 2 days to afford Compound 144•tartate salt (258 mg, 87% yield) as a white solid. 1H NMR (DMSO-d6, 300 MHz) δ 7.46-7.44 (d, J=8.8 Hz, 1H), 6.77 (s, 1H), 6.76-6.71 (m, 2H), 4.17-4.09 (s, 4H), 4.08-4.03 (m, 1H), 3.93 (s, 1H), 2.94-2.90 (m, 1H), 2.88-2.60 (m, 4H), 2.58-2.54 (m, 1H), 1.74 (m, 4H); MS (ESI) 421.2 [(M+H)+].

Example 10

N-((1R,2R)-1-(2,3-Dihydrobenzo[b][1,4]dioxin-6-yl)-1-hydroxy-3-(pyrrolidin-1-yl-d8)propan-2-yl-1-d)octanamide hemi-L-tartaric acid salt (Compound 143•tartate salt)

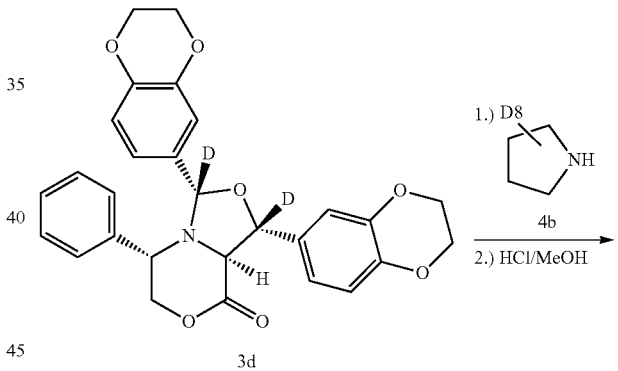

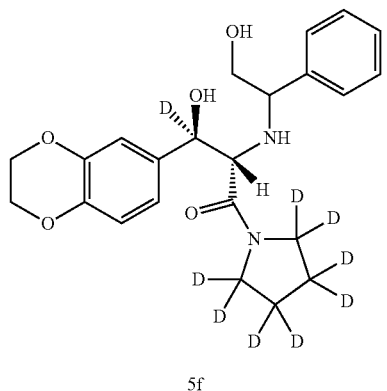

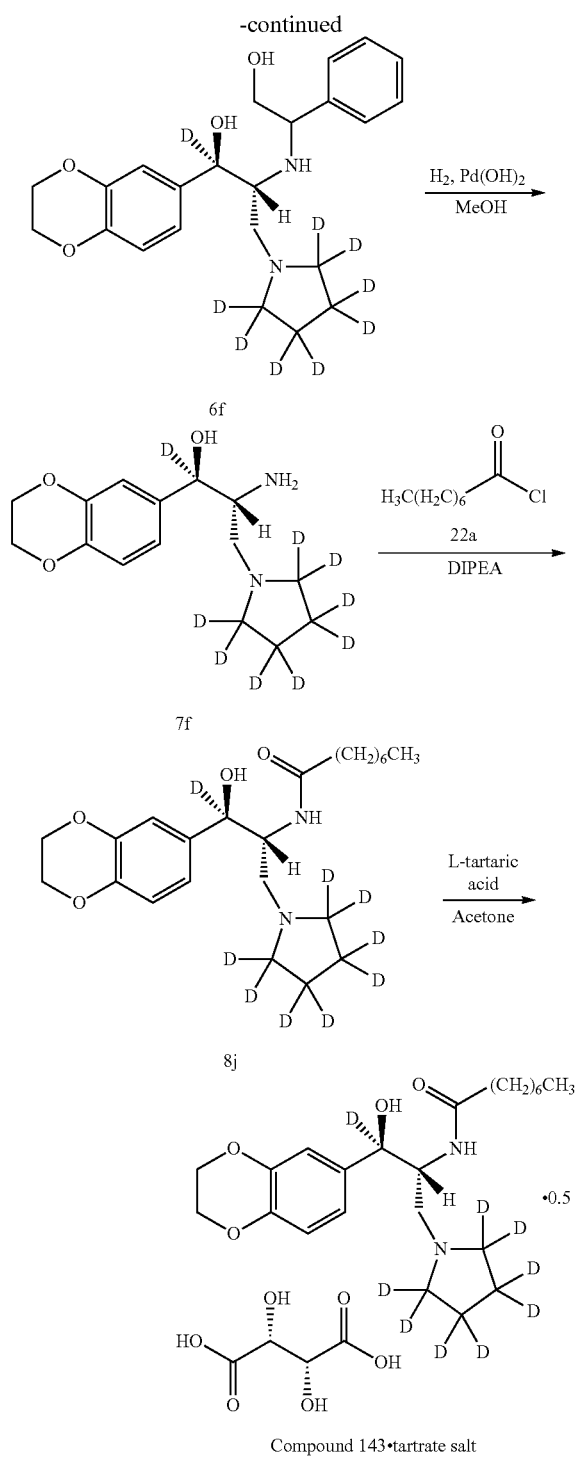

Compound 143·tartrate salt

Step 1. (2S,3R)-3-(2,3-Dihydrobenzo[b][1,4]dioxin-6-yl)-3-hydroxy-2-(2-hydroxy-1-phenylethyl) amino)-1-(pyrrolidin-1-yl-d8)propan-1-one-3-d (5f)

Pyrrolidine-$d_8$ (4b) (2.25 g, 28.3 mmol, CDN Isotopes, 98 atom % D) was added to a solution of 3d (2.77 g, 5.66 mmol) in dichloromethane (35 mL). The mixture was stirred at room temperature overnight, concentrated under reduced pressure and the residue was dissolved in methanol (20 mL) and concentrated under reduced pressure (process repeated 2x). The residual yellow oil was dissolved in mixture of methanol (32 mL) and 1M HCl (32 mL) and the reaction was refluxed for 4 hours, cooled to room temperature and concentrated under reduced pressure. Ethyl acetate (70 mL) was added and the mixture stirred for 30 minutes. The layers were separated and the organic layer was extracted with 1M HCl (75 mL). The combined aqueous layer was washed twice with ethyl acetate (2x45 mL) and the pH of the aqueous layer was adjusted with 1M NaOH to pH 4, then with saturated sodium bicarbonate solution to pH 8. The aqueous mixture was extracted three times with ethyl acetate (3x80 mL). The combined organic layer was washed with saturated sodium chloride (40 mL), dried over sodium sulfate, filtered, and concentrated under reduced pressure to give 5f (2.16 g, 91% yield) as a yellow foam which was taken directly to the next step without further purification.

Step 2. (1R,2R)-1-(2,3-Dihydrobenzo[b][1,4]dioxin-6-yl)-2-((2-hydroxy-1-phenylethyl)amino)-3-(pyrrolidin-1-yl-d8)propan-1-d-1-ol (6f)

To a solution of compound 5f (2.16 g, 5.12 mmol) in anhydrous THF (30 mL) at 0° C. was added a 1.0M solution of lithium aluminum hydride in THF (12.8 mL, 12.8 mmol). The mixture was stirred at room temperature for 20 hours. Additional 1.0M lithium aluminum hydride solution in THF (4.6 mL, 4.6 mmol, 0.9 equiv) was added, and the mixture further stirred at room temperature for 24 hours. The mixture was cooled to 0° C. and quenched with 10% NaOH and diluted with water (30 mL), and extracted with ethyl acetate (3x70 mL). The combined organic layer was washed with saturated sodium chloride (20 mL), dried over sodium sulfate, filtered and concentrated under reduced pressure to give 6f (1.80 g, 86% yield) as a yellow oil, which was taken directly to the next step without further purification.

Step 3. (1R,2R)-2-Amino-1-(2,3-dihydrobenzo[b][1,4]dioxin-6-yl)-3-(pyrrolidin-1-yl-d8)propan-1-d-1-ol (7f)

To a solution of 6f (1.80 g, 4.41 mmol) in methanol (40 mL) was added palladium hydroxide on carbon (240 mg), trifluoroacetic acid (5 mL), and water (4 mL) and the mixture was stirred under hydrogen (50 psi) for 24 hours at room temperature. The mixture was filtered through a bed of celite, washed with methanol, and concentrated under reduced pressure. Water (60 mL) was added and the aqueous solution was washed with ethyl acetate (3x30 mL) and the aqueous layer adjusted to pH 12 with a 24% NaOH, and extracted with dichloromethane (3x60 mL). The combined organic layer was dried over sodium sulfate, filtered and concentrated under reduced pressure. The residual material was dissolved in chloroform (20 mL), concentrated under reduced pressure and dried in a vacuo at room temperature to afford 7f (0.88 g, 69% yield) as a colorless oil, which was taken directly to the next step without further purification.

Step 4. N-(1R,2R)-1-(2,3-Dihydrobenzo[b][1,4]dioxin-6-yl)-1-hydroxy-3-(pyrrolidin-1-yl-d8)propan-2-yl-1-d)octanamide (8j)

To a solution of 7f (0.44 g, 1.53 mmol) and diisopropylethylamine (0.25 mL, 1.45 mmol) in dichloromethane (20 mL) at 0° C. was added dropwise 22a (0.21 mL, 1.22 mmol). The mixture was stirred at 0° C. for 4 hours and 10% NaOH (15 mL) was added and the biphasic mixture was stirred for 30 minutes. The layers were separated and the aqueous layer was extracted with dichloromethane (3×30 mL). The combined organic layer was dried over sodium sulfate, filtered and concentrated under reduced pressure, and the residue was purified by reverse phase chromatography on an AnaLogix automated chromatography system, eluting with a gradient of 0 to 50% acetonitrile in water. Product fractions were pooled and evaporated in vacuo to afford 8j (0.25 g, 40% yield) as an off-white solid.

Step 5. N-(1R,2R)-1-(2,3-Dihydrobenzo[b][1,4]dioxin-6-yl)-1-hydroxy-3-(pyrrolidin-1-yl-d8)propan-2-yl-1-d)octanamide hemi-L-tartaric acid salt (Compound 143•tartate salt)

L-tartaric acid (45.4 mg, 0.30 mmol) was dissolved in acetone (1 mL) at 55° C. and was added to a solution of 8j (250 mg, 0.60 mmol, 1 equiv) in acetone (3.5 mL) at room temperature, and the mixture was stirred at room temperature for 10 minutes, 55° C. for 10 minutes, and room temperature for 1 hour during which time a white precipitate formed. The solid was filtered, washed with cold acetone (3 mL) and dried in a vacuo at room temperature for 2.5 days to afford Compound 143•tartate salt (220 mg, 75% yield) as a white solid. 1H NMR (DMSO-d6, 300 MHz) δ7.53-7.51 (d, J=9.1 Hz, 1H), 6.77 (s, 1H), 6.76-6.71 (m, 2H), 4.17-4.10 (s, 4H), 4.09-4.04 (m, 1H), 3.91 (s, 1H), 2.96-2.90 (m, 1H), 2.64-2.57 (m, 1H), 2.04-1.94 (m, 2H), 1.37-1.04 (m, 10H), 0.86-0.81 (m, 3); MS (ESI) 414.3 [(M+H)+].

Example 11

N-(1R,2R)-1-(2,3-Dihydrobenzo[b][1,4]dioxin-6-yl)-1-hydroxy-3-(pyrrolidin-1-yl)propan-2-yl-3,3-d2)octanamide hemi-L-tartaric acid salt (Compound 170•tartrate salt)

Scheme 7a. Preparation of Compound 170•tartrate salt

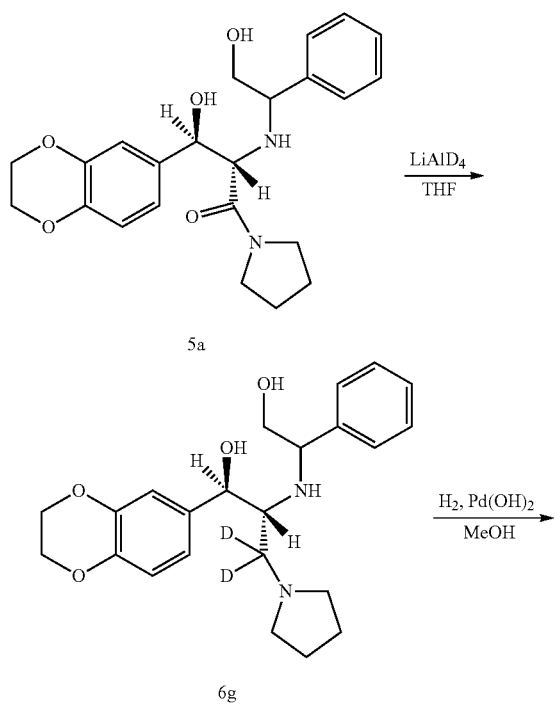

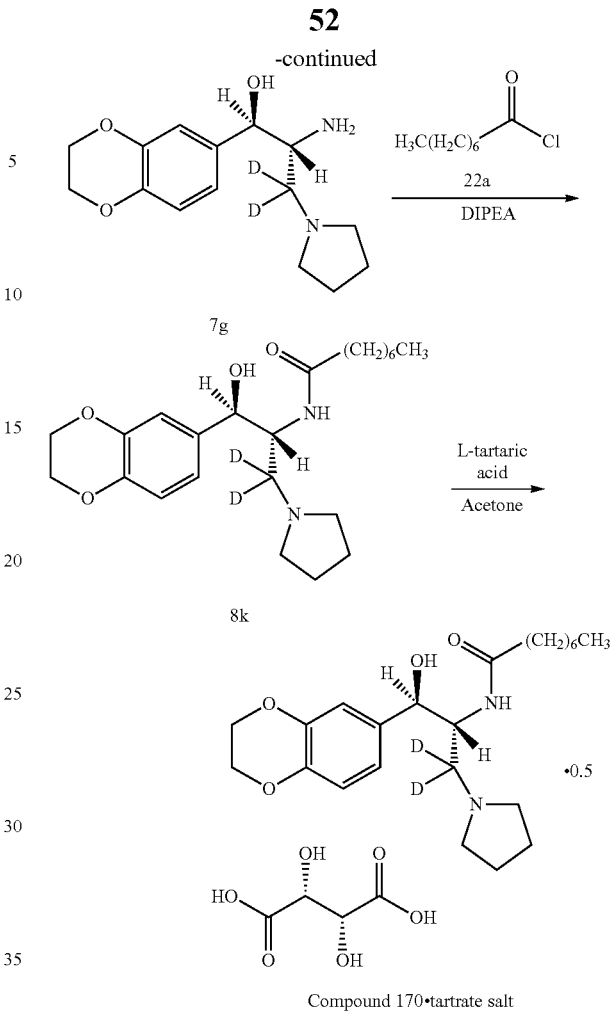

Compound 170•tartrate salt

Step 1. (1R,2R)-1-(2,3-Dihydrobenzo[b][1,4]dioxin-6-yl)-2-((2-hydroxy-1-phenylethyl)amino)-3-(pyrrolidin-1-yl)propan-3,3-d2-1-ol (6g)

To a solution of compound 5a (1.78 g, 4.31 mmol) in anhydrous THF (25 mL) at 0° C. was added Lithium aluminum deuteride (0.45 g, 10.8 mmol, Armar Chemicals, 98 atom % D). The mixture was stirred at room temperature for 20 hours, cooled to 0° C. and additional lithium aluminum deuteride (0.20 g, 4.8 mmol) was added and stirred at room temperature for 24 hours. Further analysis indicated incomplete reaction and the mixture was heated at 50° C. for 2 hours, cooled to 0° C., and quenched with 10% NaOH. The mixture was diluted with water (30 mL), and filtered and the filtrate extracted with ethyl acetate (3×60 mL). The combined organic layer was washed with saturated sodium chloride (20 mL), dried over sodium sulfate, filtered and concentrated under reduced pressure to afford 6g (1.64 g, 95% yield) as a yellow foam, which was taken directly to the next step without further purification.

Step 2. (1R,2R)-2-Amino-1-(2,3-dihydrobenzo[b][1,4]dioxin-6-yl)-3-(pyrrolidin-1-yl)propan-3,3-d2-1-ol (7g)

To a solution of 6g (1.64 g, 4.09 mmol) in methanol (40 mL) was added, palladium hydroxide on carbon (220 mg), trifluoroacetic acid (5 mL), and water (4 mL) and the mixture was stirred under hydrogen (50 psi) at room temperature for 16 hours. The mixture was filtered through a bed of celite, washed with methanol, and the filtrate was concentrated under reduced pressure. Water (40 mL) was added, and the aqueous solution was washed with ethyl acetate (3×25 mL). The aqueous layer was adjusted to pH 12 with 24% NaOH, extracted with dichloromethane (3×40 mL) and the combined organic layers were dried over sodium sulfate, filtered and concentrated under reduced pressure. The resulting residue was dissolved in chloroform (20 mL), concentrated under reduced pressure and dried in a vacuo at room temperature to afford 7g (0.84 g, 73% yield) as a yellow foam, which was taken directly to the next step without further purification.

Step 3. N-(1R,2R)-1-(2,3-Dihydrobenzo[b][1,4]dioxin-6-yl)-1-hydroxy-3-(pyrrolidin-1-yl)propan-2-yl-3,3-d2)octanamide (8k)

To a solution of 7g (0.39 g, 1.40 mmol) and diisopropylethylamine (0.23 mL, 1.33 mmol) in dichloromethane (10 mL) at 0° C. was added dropwise a solution of 22a (0.19 mL, 1.12 mmol) in dichloromethane (5 mL) and the mixture was stirred at 0° C. for 2 hours, and at room temperature for 1 hour. 10% NaOH (15 mL) was added and the biphasic mixture was stirred for 30 minutes. The layers were separated and the aqueous layer was extracted with dichloromethane (3×25 mL), and the combined organic layer was dried over sodium sulfate, filtered and concentrated under reduced pressure. The residue was purified by reverse phase chromatography on an AnaLogix automated chromatography system (55 g), eluting with a gradient of 0 to 50% acetonitrile in water. Product fractions were pooled and evaporated in vacuo to afford 8k (0.23 g, 41% yield) as a colorless oil.

Step 4. N-(1R,2R)-1-(2,3-Dihydrobenzo[b][1,4]dioxin-6-yl)-1-hydroxy-3-(pyrrolidin-1-yl)propan-2-yl-3,3-d2)octanamide hemi-L-tartaric acid salt (Compound 145•tartrate salt)

L-tartaric acid (43 mg, 0.29 mmol) was dissolved in acetone (1 mL) at 55° C. and was added to a solution of 8k (234 mg, 0.58 mmol) in acetone (3 mL) at room temperature, and the mixture was stirred at room temperature for 30 minutes, 55° C. for 10 minutes, room temperature for 30 minutes and at 0° C. for 2 hours during which time a white solid resulted. The solid was filtered, washed with cold acetone (3 mL) and dried in a vacuo at room temperature for 4 days to give Compound 170•tartrate salt (186 mg, 67% yield) as a white solid. 1H NMR (DMSO-$d_6$, 300 MHz) δ 7.46-7.44 (d, J=8.5 Hz, 1H), 6.76 (s, 1H), 6.71 (m, 2H), 4.66-4.65 (d, J=2.9 Hz, 1H), 4.17-4.07 (s, 4H), 4.06-4.03 (m, 1H), 3.92 (s, 1H), 2.72 (m, 4H), 2.03-1.97 (m, 2H), 1.73 (m, 4H), 1.08-1.35 (m, 10H), 0.86-0.82 (m, 3H); MS (ESI) 407.1 [(M+H)+].

Example 12

N-((1R,2R)-1-(2,3-dihydrobenzo[b][1,4]dioxin-6-yl)-1-hydroxy-3-(pyrrolidin-2-yl-3,3-d2)octan-d15-amide hemi-L-tartaric acid salt (Compound 171•tartrate salt)

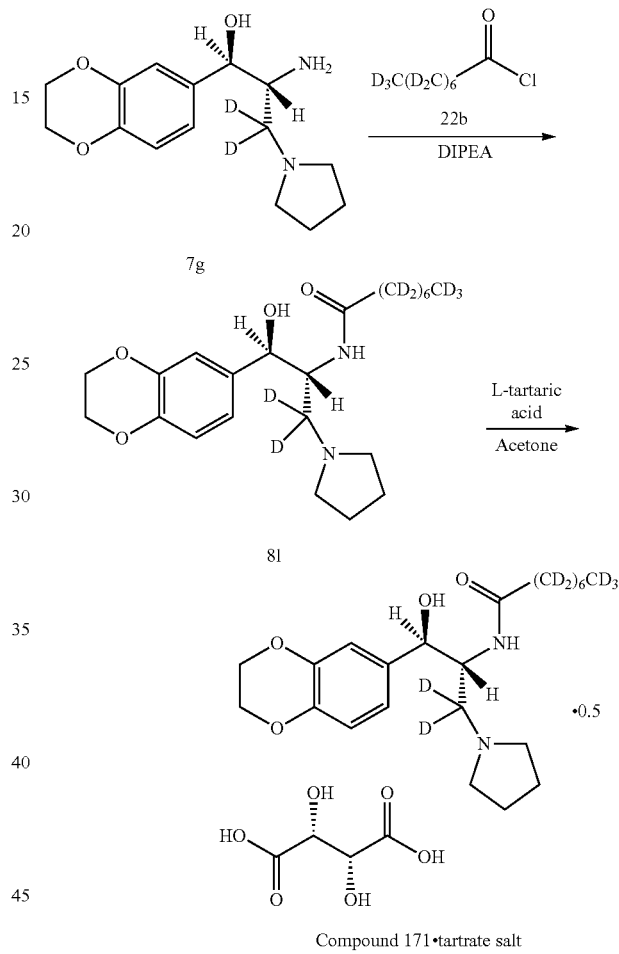

Scheme 7b. Preparation of Compound 171•tartrate salt

Step 1. N-(1R,2R)-1-(2,3-Dihydrobenzo[b][1,4]dioxin-6-yl)-1-hydroxy-3-(pyrrolidin-2-yl-3,3-d2)octan-d15-amide (8l)

To a solution of 7g (0.41 g, 1.46 mmol) and diisopropylethylamine (0.24 mL, 1.39 mmol) in dichloromethane (15 mL) at 0° C. was added dropwise a solution of 22b (0.21 g, 1.17 mmol) in dichloromethane (5 mL). The mixture was stirred at 0° C. for 2 hours and at room temperature for 1 hour. 10% NaOH (15 mL) was added and the biphasic mixture was stirred for 30 minutes. The layers were separated and the aqueous layer was extracted with dichloromethane (3×25 mL). The combined organic layer was dried over sodium sulfate, filtered, and concentrated under reduced pressure. The residue was purified by reverse phase chromatography on an AnaLogix automated chromatography system eluting with a gradient of 0 to 50% acetonitrile in water. Product fractions were pooled and evaporated in vacuo to afford 8l (0.24 g, 39% yield) as a colorless oil.

Step 2. N-(1R,2R)-1-(2,3-dihydrobenzo[b][1,4]dioxin-6-yl)-1-hydroxy-3-(pyrrolidin-1-yl)propan-2-yl-3,3-d2)octan-d15-amide hemi-L-tartaric acid salt (Compound 171•tartrate salt)

L-tartaric acid (42 mg, 0.28 mmol) was dissolved in acetone (1 mL) at 55° C. and was added to a solution of 8l (235 mg, 0.56 mmol) in acetone (3 mL) at room temperature. The mixture was stirred at room temperature for 30 minutes, 55° C. for 10 minutes, room temperature for 30 minutes and 0° C. for 2 hours during which time a white solid resulted. The solid was filtered, washed with cold acetone (3 mL) and dried in a vacuo at room temperature for 5 days to afford Compound 171•tartrate salt (237 mg, 86% yield) as a white solid. $^1$H NMR (DMSO-$d_6$, 300 MHz) δ7.44-7.41 (d, J=9.1 Hz, 1H), 6.78 (s, 1H), 6.73-6.72 (m, 2H), 4.67-4.66 (d, J=2.6 Hz, 1H), 4.19 (s, 4H), 4.09-4.05 (m, 1H), 3.93 (s, 1H), 2.74-2.51 (m, 4H), 1.75 (m, 4H); MS (ESI) 422.2 [(M+H)+].

Example 13

Evaluation of Metabolic Stability in Human CYP2D6 Supersomes™

SUPERSOMES™ Assay.
Materials: CYP2D6 Supersomes™ were obtained from Corning Gentest. β-nicotinamide adenine dinucleotide phosphate, reduced form (NADPH), magnesium chloride ($MgCl_2$), and dimethyl sulfoxide (DMSO) were purchased from Sigma-Aldrich. D-Eliglustat compounds were supplied by Concert Pharmaceuticals.

Determination of Metabolic Stability: 10 mM stock solutions of test compounds were prepared in DMSO. 7.5 mM dosing solutions were diluted to 12.75 μM in acetonitrile (ACN). The CYP2D6 supersomes were diluted to 5 pmol/mL in 0.1 M potassium phosphate buffer, pH 7.4, containing 3 mM $MgCl_2$. The diluted supersomes were added to wells of a 96-well deep-well polypropylene plate in triplicate. A 10 μL aliquot of the 12.75 μM test compound was added to the supersomes and the mixture was pre-warmed for 10 minutes. Reactions were initiated by addition of pre-warmed NADPH solution. The final reaction volume was 0.5 mL and contained 5 pmol/mL CYP2D6 supersomes, 0.25 μM test compound, and 2 mM NADPH in 0.1 M potassium phosphate buffer, pH 7.4, and 3 mM $MgCl_2$. The reaction mixtures were incubated at 37° C. and 50 μL aliquots were removed at 0, 5, 10, 20, and 30 minutes and added to shallow-well 96-well plates which contained 50 μL of ice-cold ACN with internal standard to stop the reactions. The plates were stored at 4° C. for 20 minutes after which 100 μL of water was added to the wells of the plate before centrifugation to pellet precipitated proteins. Supernatants were transferred to another 96-well plate and analyzed for amounts of parent remaining by LC-MS/MS using an Applied Bio-systems mass spectrometer.

Data analysis: The in vitro $t_{1/2}$s for test compounds were calculated from the slopes of the linear regression of % parent remaining (ln) vs incubation time relationship.

in vitro $t_{1/2}$=0.693/k k=−[slope of linear regression of % parent remaining (ln) vs incubation time]

Data analysis was performed using Microsoft Excel Software.

TABLE 4a

Metabolic Stability of Compounds of the Invention versus Eliglustat in Human CYP2D6 Supersomes™

| Compound | $t_{1/2}$ (minutes) | | |
|---|---|---|---|
| | Experiment 1 | Experiment 2 | Ave ± SD (% Δ) |
| Eliglustat (D0) | 6.6 | 5.1 | 6.7 ± 1.5 |
| 102 | 11.4 | 11.9 | 11.7 ± 0.3 75% |
| 112 | 6.2 | 4.7 | 5.4 ± 1.1 |
| 103 | 5.9 | 4.8 | 5.4 ± 0.8 |
| 118 | 5.6 | 5.9 | 5.8 ± 0.2 |
| 105 | 13.0 | 17.5 | 15.2 ± 3.2 127% |
| 114 | 12.9 | 11.0 | 12.0 ± 1.4 79% |
| 120 | 16.6 | 13.8 | 15.2 ± 2.0 127% |
| 142 | 5.9 | 7.0 | 6.5 ± 0.8 |
| 143 | 6.0 | 9.7 | 7.9 ± 2.6 18% |
| 144 | 12.3 | 12.6 | 12.5 ± 0.2 87% |
| 170 | 7.0 | 8.1 | 7.5 ± 0.8 |
| 171 | 12.3 | 17.1 | 14.7 ± 3.4 119% |

*% Δ = [(deuterated species) − (nondeuterated species)](100)/(nondeuterated species)

TABLE 4b

Metabolic Stability of Compounds of the Invention versus Eliglustat in Human CYP2D6 Supersomes™

| Compound | $t_{1/2}$ (minutes) | | |
|---|---|---|---|
| | Experiment 1 | Experiment 2 | Ave ± SD (% Δ) |
| Eliglustat (D0) | 9.7 | 6.3 | 8.0 ± 2.4 |
| 103 | 8.5 | 5.7 | 7.1 ± 2.0 |
| 114 | 17.4 | 11.8 | 14.6 ± 4.0 83% |
| 120 | 21.5 | 15.5 | 18.5 ± 4.2 131% |

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay:
The metabolic stability of compounds of Formula I, Ia, Ib and Ic is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures:

Human liver microsomes are obtained from a commercial source (e.g., Absorption Systems L.P. (Exton, Pa.)). The incubation mixtures are prepared as follows:

Reaction Mixture Composition

| Liver Microsomes | 1.0 mg/mL |
|---|---|
| NADPH | 1 mM |
| Potassium Phosphate, pH 7.4 | 100 mM |
| Magnesium Chloride | 10 mM |
| Test Compound | 1 µM. |

Incubation of Test Compounds with Liver Microsomes:

The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 µM. An aliquot of the reaction mixture is prepared as a blank control, by the addition of plain organic solvent (not the test compound). The reaction is initiated by the addition of cofactors (not into the negative controls), and then incubated in a shaking water bath at 37° C. Aliquots (200 µL) are withdrawn in triplicate at multiple time points (e.g., 0, 15, 30, 60, and 120 minutes) and combined with 800 µL of ice-cold 50/50 acetonitrile/dH$_2$O to terminate the reaction. The positive controls, testosterone and propranolol, as well as eliglustat, are each run simultaneously with the test compounds in separate reactions.

All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

We claim:

1. A compound of Formula I:

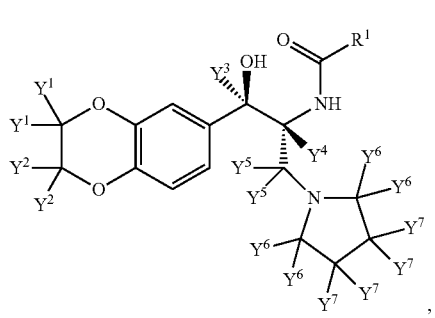

(I)

or a pharmaceutically acceptable salt thereof, wherein
each $Y^1$ is the same and is hydrogen or deuterium;
each $Y^2$ is the same and is hydrogen or deuterium;
$Y^3$ is hydrogen or deuterium;
$Y^4$ is hydrogen or deuterium;
each $Y^5$ is the same and is hydrogen or deuterium;
each $Y^6$ is the same and is hydrogen or deuterium;
each $Y^7$ is the same and is hydrogen or deuterium;
$R^1$ is —(CD$_2$)$_6$CD$_3$; and wherein
each designated deuterium atom has a deuterium incorporation of at least 45%.

2. The compound of claim 1, wherein each $Y^1$ is hydrogen.

3. The compound of claim 1, wherein each $Y^1$ is deuriutn.

4. The compound of claim 1, 2 or 3, wherein each $Y^2$ is hydrogen.

5. The compound of claim 1, 2 or 3, wherein each $Y^2$ is deuterium.

6. The compound of claim 1, wherein $Y^3$ is hydrogen.

7. The compound of claim 1, wherein $Y^3$ is deuterium.

8. The compound of claim 6 or 7, wherein $Y^4$ is hydrogen.

9. The compound of claim 6 or 7, wherein $Y^4$ is deuterium.

10. The compound of claim 1, wherein each $Y^7$ is hydrogen.

11. The compound of claim 1, wherein each $Y^7$ is deuterium.

12. The compound of claim 1, wherein each $Y^5$ is the same as each $Y^6$.

13. The compound of claim 1, wherein the compound is selected from any one of the compounds in the table below:

| Compound | each $Y^1$ = each $Y^2$ | each $Y^3$ = each $Y^4$ | $Y^5$ | $Y^6$ | $Y^7$ | $R^1$ |
|---|---|---|---|---|---|---|
| 102 | H | H | H | H | H | —(CD$_2$)$_6$—CD$_3$ |
| 105 | D | H | H | H | H | —(CD$_2$)$_6$—CD$_3$ |
| 108 | H | D | H | H | H | —(CD$_2$)$_6$—CD$_3$ |
| 111 | H | H | H | H | D | —(CD$_2$)$_6$—CD$_3$ |
| 114 | H | H | H | D | D | —(CD$_2$)$_6$—CD$_3$ |
| 117 | H | H | D | D | D | —(CD$_2$)$_6$—CD$_3$ |
| 182 | D | D | H | H | H | —(CD$_2$)$_6$—CD$_3$ |
| 185 | D | H | H | H | D | —(CD$_2$)$_6$—CD$_3$ |
| 120 | D | H | H | D | D | —(CD$_2$)$_6$—CD$_3$ |
| 123 | D | H | D | D | D | —(CD$_2$)$_6$—CD$_3$ |
| 126 | H | D | H | H | D | —(CD$_2$)$_6$—CD$_3$ |
| 129 | H | D | H | D | D | —(CD$_2$)$_6$—CD$_3$ |
| 132 | H | D | D | D | D | —(CD$_2$)$_6$—CD$_3$ |
| 135 | D | H | H | H | D | —(CD$_2$)$_6$—CD$_3$ |
| 138 | D | D | H | D | D | —(CD$_2$)$_6$—CD$_3$ |
| 141 | D | D | D | D | D | —(CD$_2$)$_6$—CD$_3$ | or a pharmaceutically acceptable salt thereof wherein any atom not designated as deuterium is present at its natural isotopic abundance.

14. The compound of claim 1, wherein any atom not designated as deuterium is present at its natural isotopic abundance.

15. A pharmaceutical composition comprising an effective amount of a compound of claim 1, or a pharmaceutically acceptable salt of said compound; and a pharmaceutically acceptable carrier.

16. A compound of claim 1, wherein the compound is selected from any one of the compounds in the table below:

| Compound | each $Y^1$ = each $Y^2$ | $Y^3$ | $Y^4$ | $Y^5$ | $Y^6$ | $Y^7$ | $R^1$ |
|---|---|---|---|---|---|---|---|
| 144 | H | D | H | H | H | H | —$(CD_2)_6$—$CD_3$ |
| 145 | D | D | H | H | H | H | —$(CD_2)_6$—$CD_3$ |
| 146 | H | D | H | H | H | D | —$(CD_2)_6$—$CD_3$ |
| 147 | H | D | H | H | D | D | —$(CD_2)_6$—$CD_3$ |
| 158 | H | D | H | D | D | D | —$(CD_2)_6$—$CD_3$ |
| 159 | D | D | H | H | H | D | —$(CD_2)_6$—$CD_3$ |
| 150 | D | D | H | H | D | D | —$(CD_2)_6$—$CD_3$ |
| 151 | D | D | H | D | D | D | —$(CD_2)_6$—$CD_3$ |
| 152 | H | D | H | H | D | H | —$(CD_2)_6$—$CD_3$ |
| 153 | H | D | H | D | D | H | —$(CD_2)_6$—$CD_3$ |
| 154 | D | D | H | H | D | H | —$(CD_2)_6$—$CD_3$ |
| 155 | D | D | H | D | D | H | —$(CD_2)_6$—$CD_3$ |
| 158 | H | H | D | H | H | H | —$(CD_2)_6$—$CD_3$ |
| 159 | D | H | D | H | H | H | —$(CD_2)_6$—$CD_3$ |
| 160 | H | H | D | H | H | D | —$(CD_2)_6$—$CD_3$ |
| 161 | H | H | D | H | D | D | —$(CD_2)_6$—$CD_3$ |
| 162 | H | H | D | D | D | D | —$(CD_2)_6$—$CD_3$ |
| 163 | D | H | D | H | H | D | —$(CD_2)_6$—$CD_3$ |
| 164 | D | H | D | H | D | D | —$(CD_2)_6$—$CD_3$ |
| 165 | D | H | D | D | D | D | —$(CD_2)_6$—$CD_3$ |
| 166 | H | H | D | H | D | H | —$(CD_2)_6$—$CD_3$ |
| 167 | H | H | D | D | D | H | —$(CD_2)_6$—$CD_3$ |
| 168 | D | H | D | H | D | H | —$(CD_2)_6$—$CD_3$ |
| 169 | D | H | D | D | D | H | —$(CD_2)_6$—$CD_3$ | or a pharmaceutically acceptable salt thereof, wherein any atom not designated as deuterium is present at its natural isotopic abundance.

17. A compound of claim 1, wherein each $Y^5$ is deuterium; each $Y^6$ is hydrogen; and the compound is selected from any one of the compounds in the table below:

| Compound | each $Y^1$ = each $Y^2$ | each $Y^3$ = each $Y^4$ | $Y^7$ | $R^1$ |
|---|---|---|---|---|
| 171 | H | H | H | —$(CD_2)_6$—$CD_3$ |
| 172 | D | H | H | —$(CD_2)_6$—$CD_3$ |
| 173 | H | H | D | —$(CD_2)_6$—$CD_3$ |
| 174 | D | H | D | —$(CD_2)_6$—$CD_3$ |
| 175 | H | D | H | —$(CH_2)_6$—$CH_3$ |
| 176 | H | D | H | —$(CD_2)_6$—$CD_3$ |
| 177 | D | D | H | —$(CD_2)_6$—$CD_3$ |
| 178 | H | D | D | —$(CD_2)_6$—$CD_3$ |
| 179 | D | D | D | —$(CD_2)_6$—$CD_3$ | or a pharmaceutically acceptable salt thereof, wherein any atom not designated as deuterium is present at its natural isotopic abundance.

18. The compound of claim 1, wherein the deuterium incorporation at each designated deuterium atom is at least 90%.

19. The compound of claim 18, wherein the deuterium incorporation at each designated deuterium atom is at least 95%.

20. The compound of claim 19, wherein the deuterium incorporation at each designated deuterium atom is at least 97%.

* * * * *